(12) United States Patent
Mori et al.

(10) Patent No.: US 7,827,148 B2
(45) Date of Patent: Nov. 2, 2010

(54) MEDICAL EQUIPMENT HAVING AUDIT LOG MANAGING FUNCTION

(75) Inventors: Kei Mori, Shioya-gun (JP); Junichi Tashiro, Otawara (JP); Megumu Fukuda, Nasushiobara (JP); Takaaki Nakano, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 960 days.

(21) Appl. No.: 11/332,217

(22) Filed: Jan. 17, 2006

(65) Prior Publication Data
US 2006/0161593 A1    Jul. 20, 2006

(30) Foreign Application Priority Data
Jan. 17, 2005  (JP)  .............................. 2005-009454
Feb. 28, 2005  (JP)  .............................. 2005-054607

(51) Int. Cl.
*G06F 17/30* (2006.01)
(52) U.S. Cl. ........................................ 707/661; 607/29
(58) Field of Classification Search .................. 707/66, 707/822; 607/1, 29
See application file for complete search history.

(56) References Cited

U.S. PATENT DOCUMENTS

| 6,314,405 | B1 * | 11/2001 | Richardson ..................... 705/3 |
|---|---|---|---|
| 7,389,144 | B1 * | 6/2008 | Osorio et al. .................. 607/29 |
| 7,454,314 | B2 * | 11/2008 | Holland et al. ............... 702/182 |
| 7,510,526 | B2 * | 3/2009 | Merry et al. ................. 600/300 |
| 2004/0249667 | A1 * | 12/2004 | Oon ............................... 705/2 |
| 2005/0061336 | A1 * | 3/2005 | Goetz et al. ................. 128/899 |
| 2005/0090754 | A1 * | 4/2005 | Wolff et al. .................. 600/509 |
| 2005/0228693 | A1 * | 10/2005 | Webb et al. ..................... 705/2 |
| 2006/0167367 | A1 * | 7/2006 | Stanczak et al. ............ 600/523 |
| 2007/0069887 | A1 * | 3/2007 | Welch et al. ........... 340/539.12 |

FOREIGN PATENT DOCUMENTS

| CN | 1554061 A | 12/2004 |
|---|---|---|
| JP | 10-283229 | 10/1998 |
| WO | WO 2004/057833 A1 | 7/2004 |

* cited by examiner

*Primary Examiner*—Debbie Le
(74) *Attorney, Agent, or Firm*—Oblon, Spivak, McClelland, Maier & Neustadt, L.L.P.

(57) ABSTRACT

A log file generating section generates an audit log file of patient information in response to various kinds of events generated in a medical equipment, and a file compressing section compresses the generated file in a local storage medium at a predetermined timing. Further, a log management section automatically transfers the compressed audit log file to an external storage device and deletes data in the local storage medium at a predetermined timing, e.g., when a remaining capacity in the local storage medium exceeds a limit value.

22 Claims, 16 Drawing Sheets

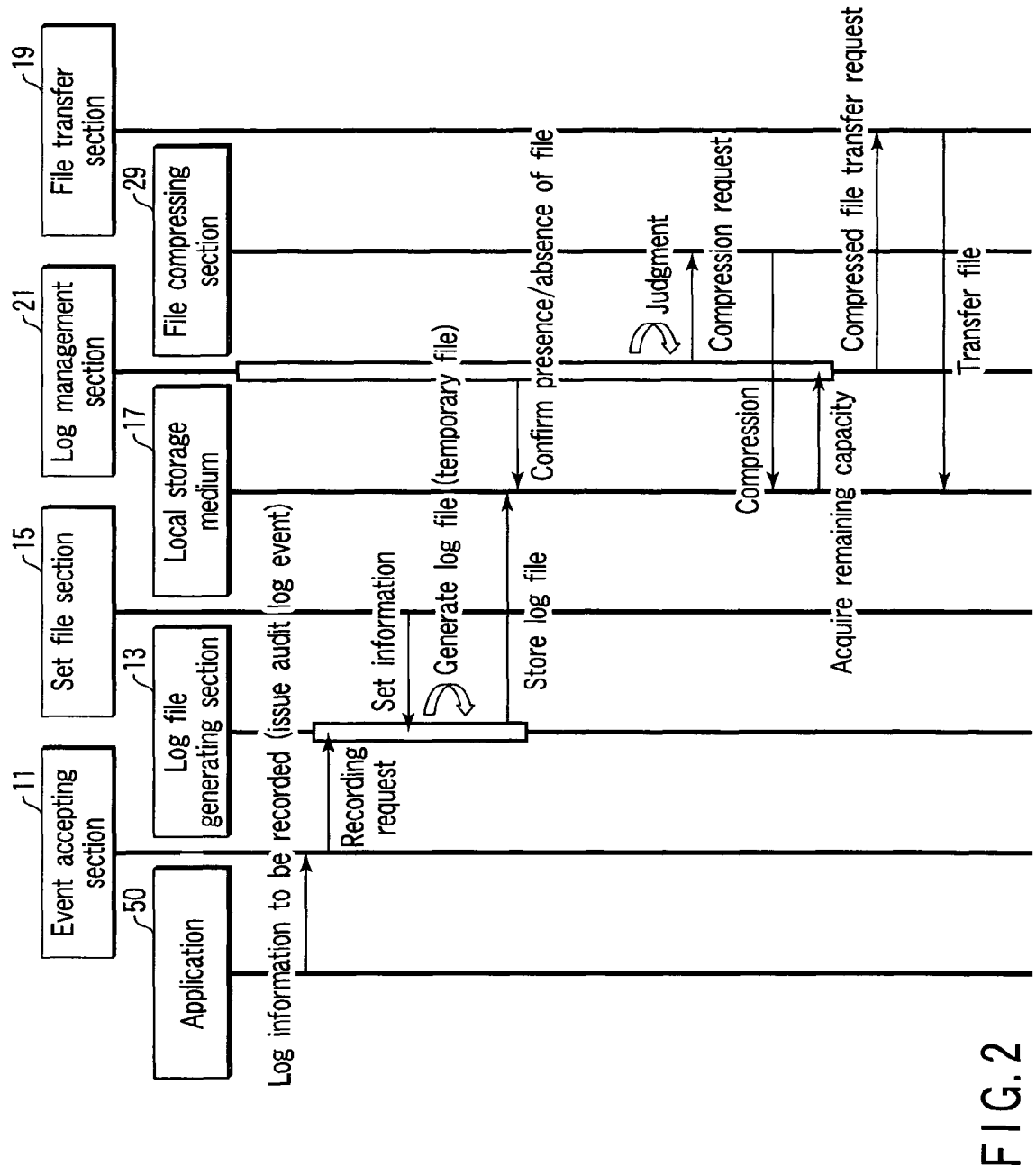
F I G. 2

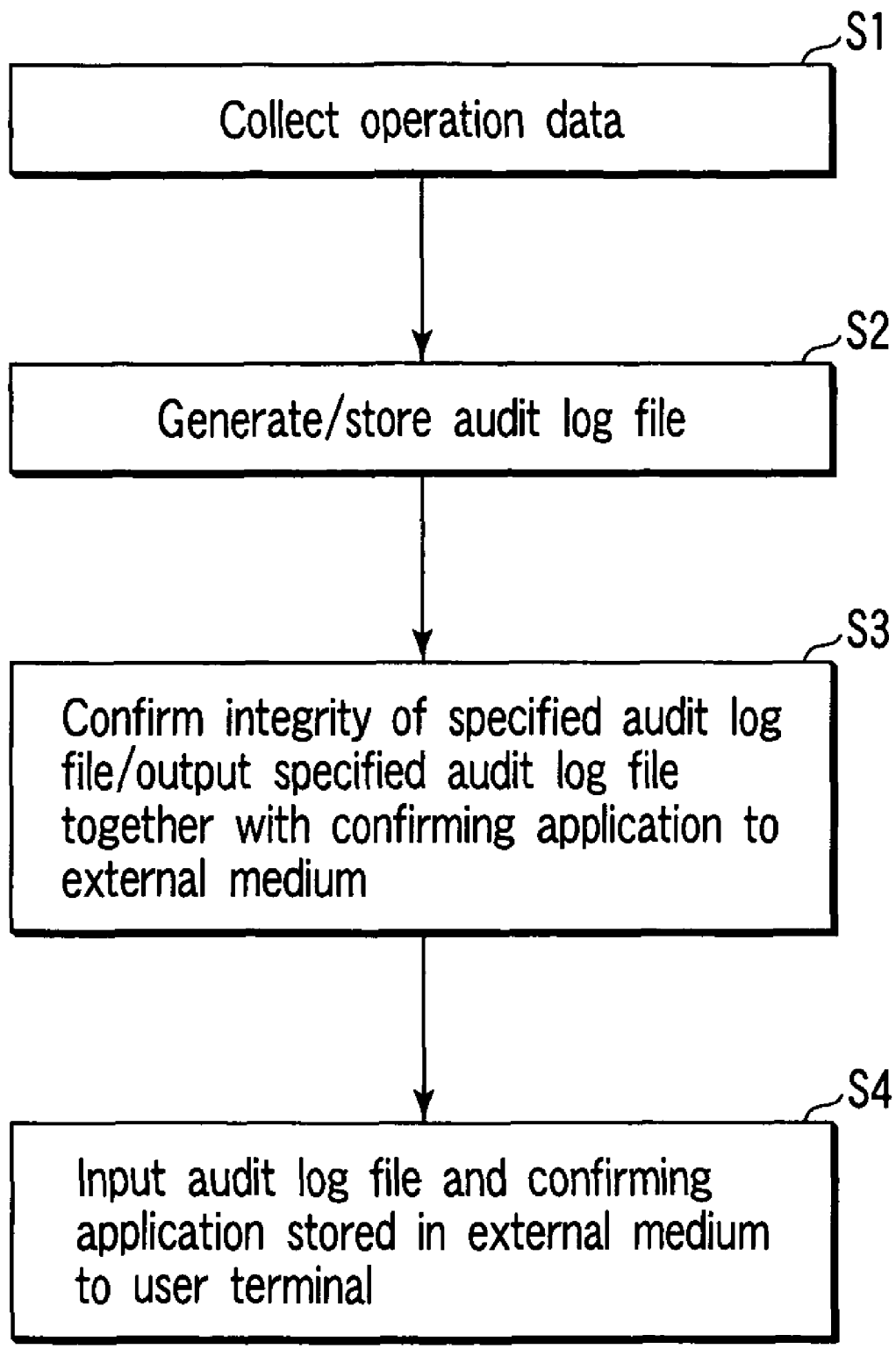
F I G. 7

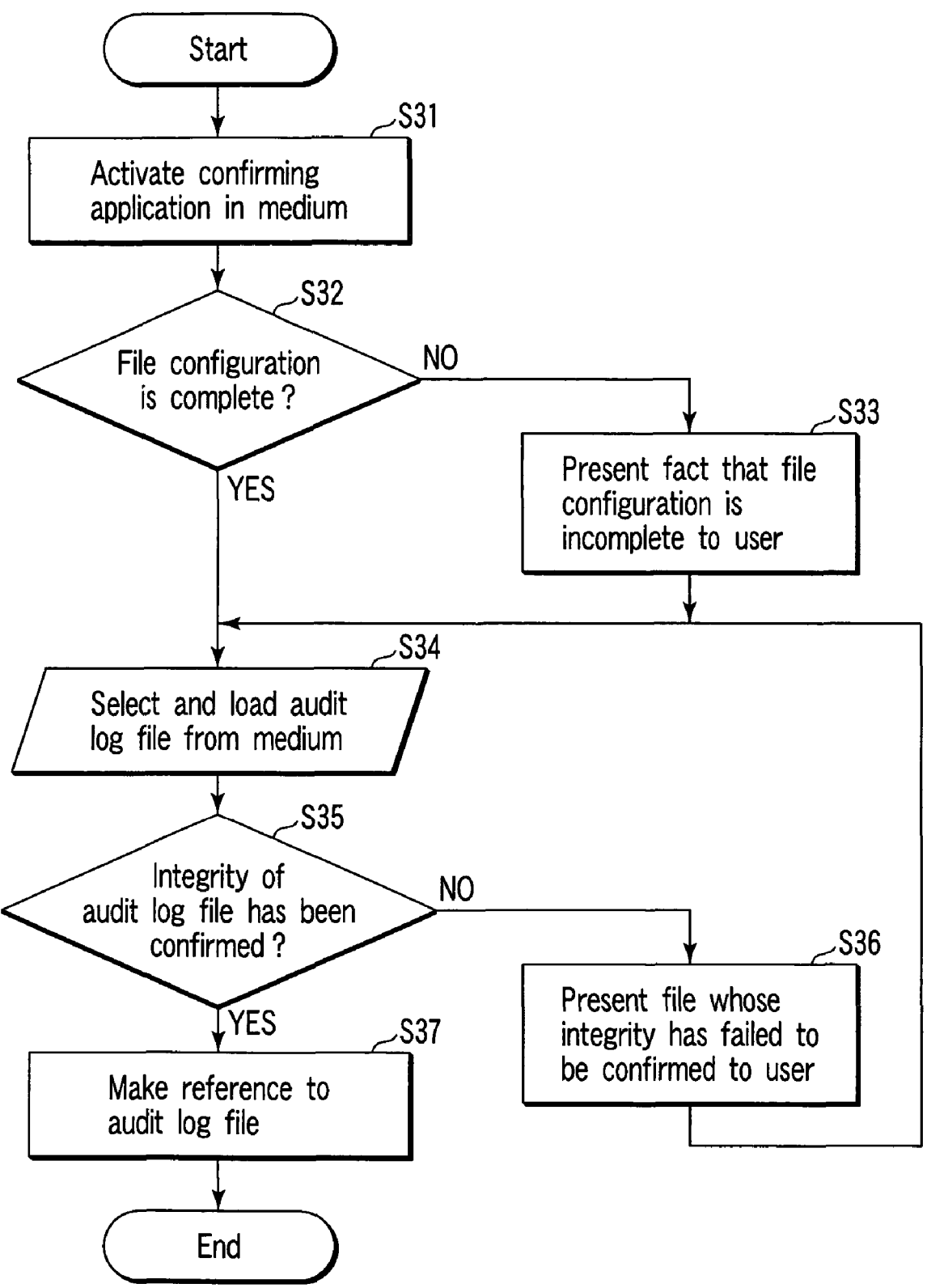
F I G. 10

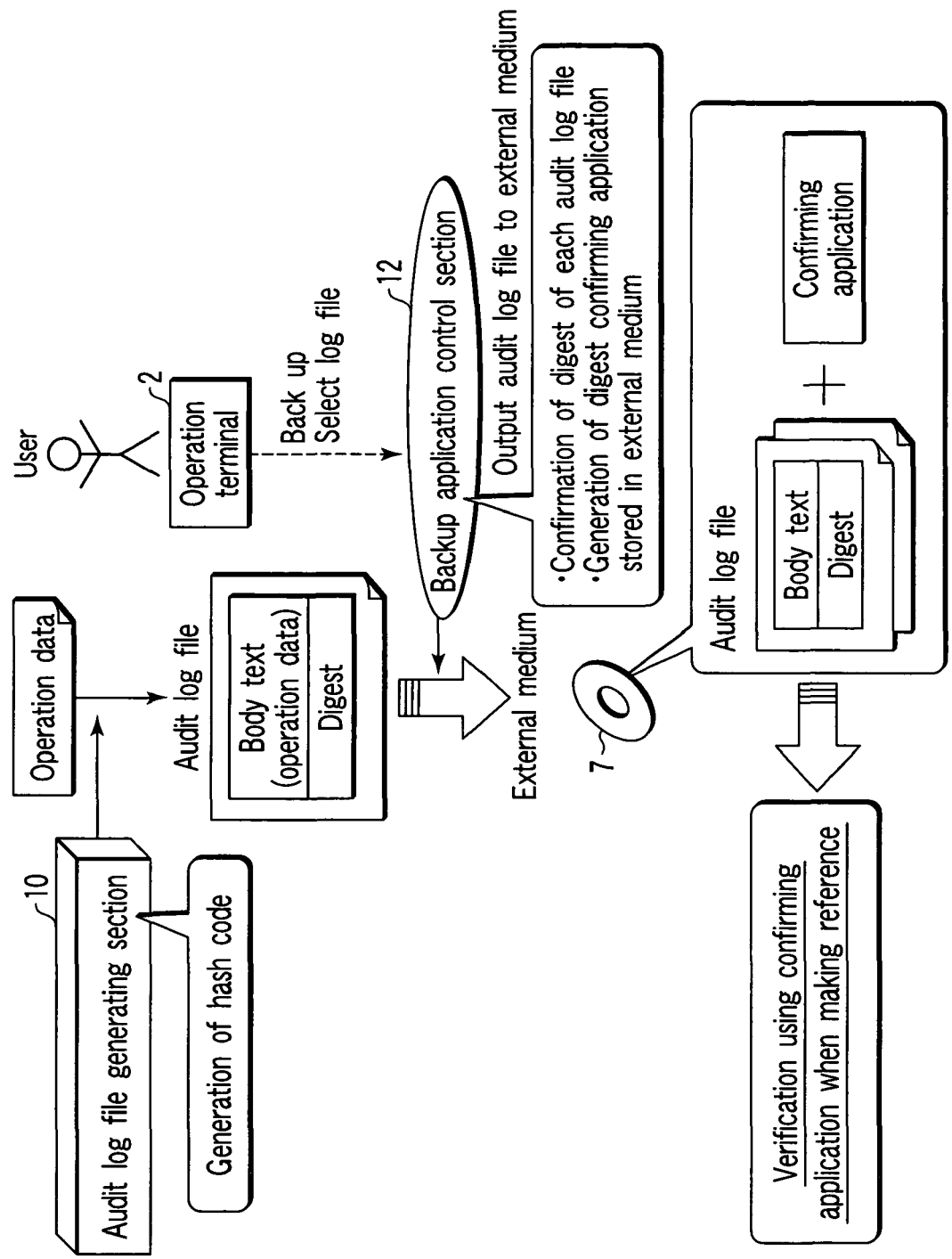
F I G. 11

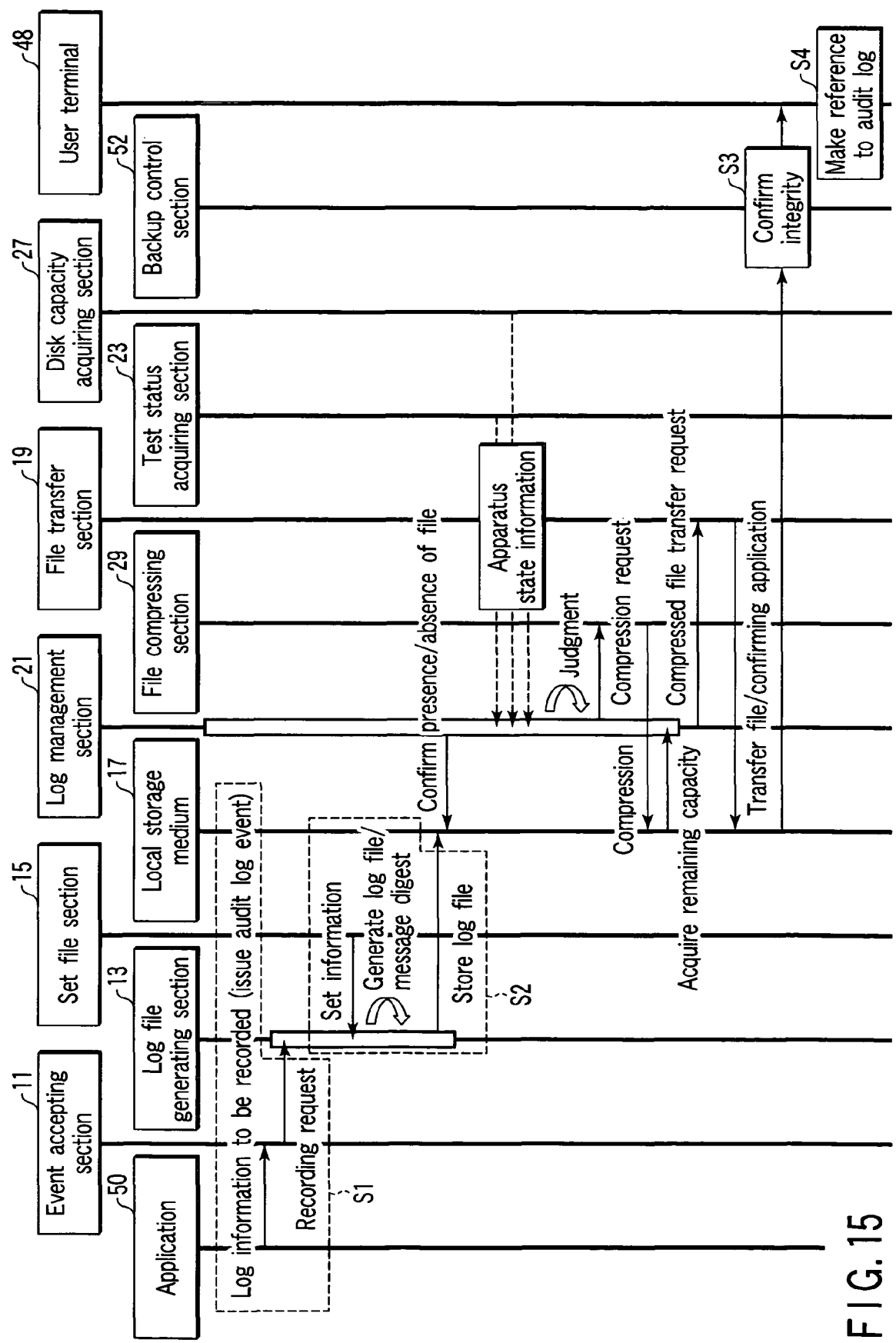
F I G. 15

MEDICAL EQUIPMENT HAVING AUDIT LOG MANAGING FUNCTION

CROSS-REFERENCE TO RELATED APPLICATIONS

This application is based upon and claims the benefit of priority from prior Japanese Patent Applications No. 2005-009454, filed Jan. 17, 2005; and No. 2005-054607, filed Feb. 28, 2005, the entire contents of both of which are incorporated herein by reference.

BACKGROUND OF THE INVENTION

1. Field of the Invention

The present invention relates to a medical equipment having an audit log managing function which records contents indicating that how and when what was carried out by who during activation of an apparatus as an audit log, saves them or transfers them to the outside in a medical equipment in a hospital.

2. Description of the Related Art

In a medical image apparatus, an operating apparatus, a laboratory test apparatus or any other medical equipment, acquired diagnostic information (image data, information concerning an operation, a test result and others) is managed by using collateral information such as a name of a patient, a patient ID, information concerning the apparatus, a disorder name, a disordered part, a test type, a date and hour of photography and others. Information constituted of the diagnostic information and the collateral information will be referred to as a patient information hereinafter. Necessary information is appropriately read from this patient information and used by a doctor who is in charge of an interpretation diagnosis, a doctor who is in charge of a pathologic diagnosis, a chief physician or the like. Each doctor additionally enters his/her remarks in an electronic medical chart or the like while, e.g., observing the read patient information, thereby realizing sharing of medical information.

In such a medical equipment, in light of protection of privacy of each patient, a history for management of the patient information, which is called an audit log, is recorded in order to verify that personal information of each patient is appropriately processed. Here, the audit log has information concerning an event which has treated the patient information in a medical equipment stored therein in, e.g., a 5W1H style, for example. Further, a file concerning the audit log is called an audit log file. The audit log file is created and then temporarily stored in an apparatus. The audit log file stored in the apparatus is periodically backed up in an external medium, transferred to an external server and managed outside the apparatus by an apparatus manager or a service engineer. The backed-up audit log file is viewed and utilized for an audit by utilizing the apparatus itself, an external computer or the like at a stage of detecting a doubtful action in a given period.

However, in management of a conventional audit log file, the following problems exist, for example.

At first, there is a possibility that a reduction in an apparatus disk capacity is provoked, collection of medical images is inhibited or a state of reducing a test throughput occurs. That is, since an access operation or the like with respect to system information or personal information of each patient during activation of the apparatus is recorded in the audit log file, its data quantity becomes enormous. As a result, a disk full state of a storage medium in the apparatus, loss of a test image, loss of an audit log, an unstable state of the system and others are provoked, which may possibly affects a test operation. Further, usually, it is often the case that an audit log to be recorded is temporarily saved in a local storage medium (in the apparatus), and this problem is of particularly note in an environment adopting this operation.

At second, an operation burden on an apparatus manager or a service engineer is large. That is, in order to avoid the disk full state of the storage medium in the apparatus, a backup operation of an audit log file must be frequently carried out, which imposes a great operation burden on the apparatus manager or the service engineer. This backup operation requires a very long time. Therefore, if an operation of performing backup when a test is not carried out is adopted, an extra duty after test hours becomes a problem. On the other hand, if an operation of performing backup simultaneously with a test is adopted, there is a possibility that a sufficient time cannot be assured for a test.

BRIEF SUMMARY OF THE INVENTION

In view of the above-described problems, it is an object of the present invention to provide a medical equipment which can avoid inhibition of collection of medical images and a reduction in a test throughput by preventing a decrease in a capacity of a storage medium in an apparatus by an audit log when storing and managing the audit log during activation of the apparatus, and can increase efficiency of an audit log backup operation by simplifying transfer of a file to the outside, thereby supporting an improvement in an operating throughput in a hospital.

According to an aspect of the present invention, there is provided a medical equipment which comprises: a log generation unit which generates a log concerning an operation of the medical equipment; and a log management unit which determines an execution timing of a log target processing which is processing using the log and giving a substantially high load to the medical equipment based on an operation state of the medical equipment, and executes the log target processing at the determined timing.

BRIEF DESCRIPTION OF THE SEVERAL VIEWS OF THE DRAWING

FIG. 2 is a flowchart showing a flow of each processing executed in audit log management in the first embodiment;

FIG. 7 is a flowchart showing a flow when an audit log is generated and the generated audit log is output to an external medium in the medical equipment depicted in FIG. 6;

FIG. 10 is a flowchart showing an example of a detailed procedure when the confirming application input from the external medium is activated to make reference to the audit log file in a user terminal depicted in FIG. 6;

FIG. 11 is a conceptual view showing an entire flow from generation of an audit log file to reference to the audit log file through an external medium in the medical equipment depicted in FIG. 6;

FIG. 15 is a flowchart showing a flow of each processing executed in audit log management in the sixth embodiment.

DETAILED DESCRIPTION OF THE INVENTION

Figure 1:
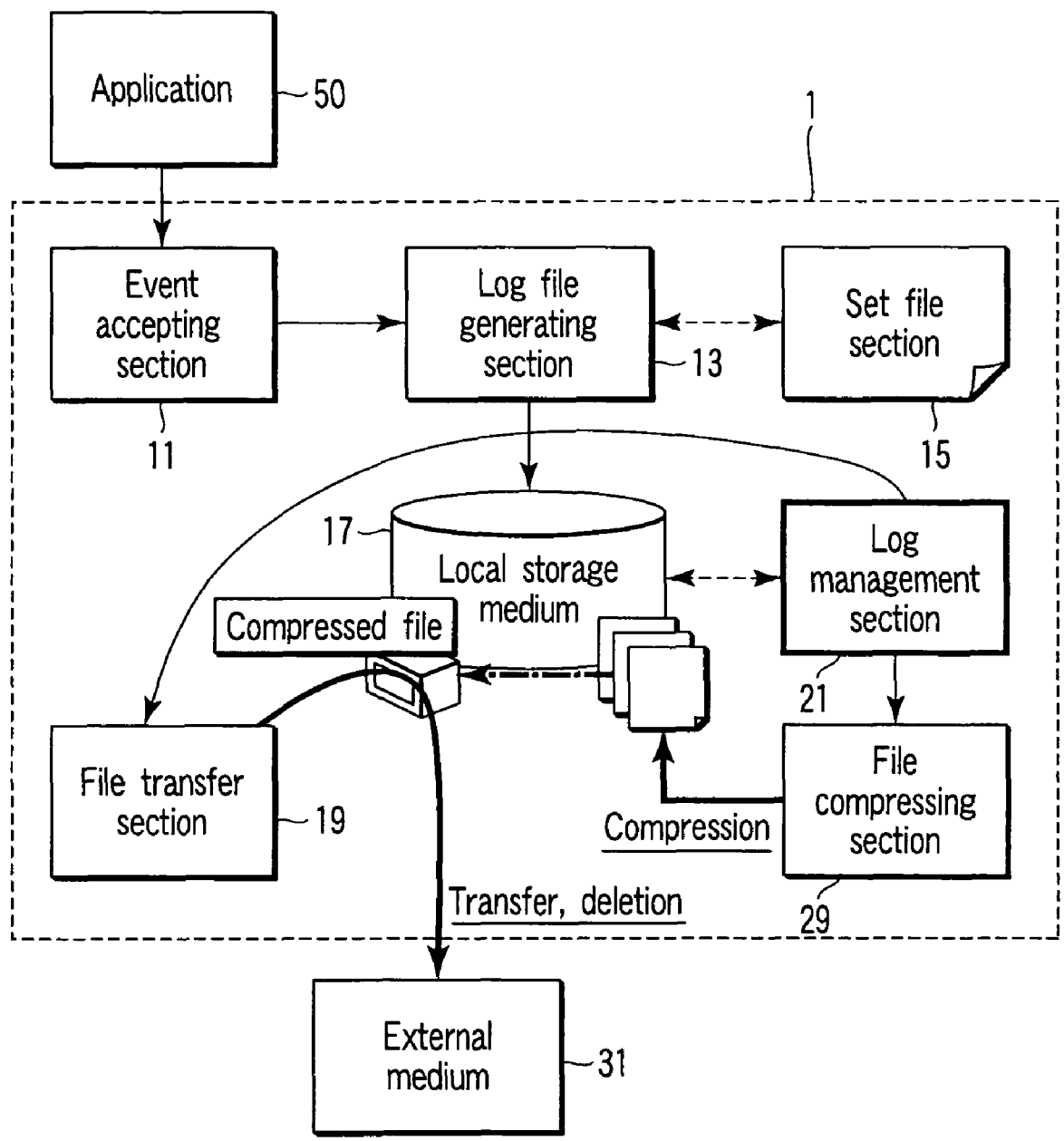
FIG. 1 is a block diagram of a medical equipment according to a first embodiment.

Audit management systems according to first to sixth embodiments of the present invention will now be described hereinafter with reference to the accompanying drawings. In the following description, like reference numerals denote constituent elements having substantially the same function and configuration, and a tautological explanation will be given as required. Further, this audit log management system is built in a computerized transverse axial tomography, an ultrasonic diagnostic equipment, a magnetic resonance imaging system, a nuclear medicine diagnostic apparatus, an operating apparatus, a laboratory test apparatus or any other medical equipment (which is not restricted to a medical image device, and includes all devices using patient information), or it is connected with the medical equipment through a network as a single equipment to be used. In each of the following embodiments, a description will be given while taking an audit log management system which is built in a medical equipment and used as an example.

It is to be noted that audit log management realized by a system according to each embodiment is processing intended for an audit log concerning an operation of a medical equipment, and controls an execution timing of processing which substantially gives a high load to the system in response to various kinds of events generated in the medical equipment. Here, as the processing which gives a high load to the system, there are, e.g., compression, transfer and encryption of an audit log, processing which generates information for verifying integrity of the audit log, processing which confirms integrity of the audit log as data, and any other processing which occupies a fixed percentage or above of a CPU when executing processing. In the following, in order to give a concrete description, an audit log is restricted to one concerning an operation in the medical equipment when dealing with patient information, and the patient information is constituted of diagnostic information and collateral information including at least a patient name (or a patient ID) and a type of a test. Therefore, when DICOM is used as a communication standard, the patient information is constituted of information concerning an image (diagnostic information) and collateral information including at least a patient name (or a patient ID) and a study (a type of a test)/a unique ID.

First Embodiment

FIG. 1 is a block diagram of a medical equipment including an audit log management system 1 according to this embodiment. As shown in the drawing, this audit log management system 1 is provided with an event accepting section 11, a log file generating section 13, a set file section 15, a local storage medium 17, a file transfer section 19, a log management section 21, a file compressing section 29 and an external medium 31.

The event accepting section 11 accepts an audit log recording request event from an application 50 of the medical equipment, and requests audit log recording to the log file generating section 13. Further, the event accepting section 11 receives system information concerning the medical equipment from the application 50, and transmits it to the log management section 21 or the like.

The log generating section 13 generates a file concerning an audit log at the time of occurrence of each event (an audit log file) in response to the audit log recording request from the event accepting section 11.

The set file section 15 stores set information which defines various kinds of conditions in audit log management. The set information in this set file section 15 can be arbitrarily changed by an input from a non-illustrated input device.

The local storage medium 17 is a storage section (e.g., a hard disk) in this audit log management system 1, which stores the audit log file generated by the log file generating section 13.

The file transfer section 19 transfers the audit log file compressed by the file compressing section 29 to the external medium 31, and deletes the transferred audit log fine in the local storage medium 17 at a predetermined timing after termination of transfer.

The log management section 21 monitors the local storage medium 17, and detects generation and storage of the audit log file. When storing the audit log file in the local storage medium 17 is detected, the log management section 21 issues a compression request to the file compressing section 29.

The file compressing section 29 compresses the audit log file generated by the log file generating section 13 at a predetermined timing. Furthermore, a compression ratio in this compression can be changed as required.

The external medium 31 stores the compressed file transferred by the file transfer section 19.

(Operation)

An operation in audit log management of this audit log management system 1 will now be described.

In audit log management by this audit log management system 1, an audit log file of patient information is generated in response to various kinds of events which have occurred in the medical equipment, and the generated audit log file is compressed in the local storage medium 17 at a predetermined timing. Furthermore, the compressed audit log file is automatically transferred to the external storage medium at a predetermined timing, e.g., when a remaining capacity in the local storage medium 17 exceeds a limit value, and data in the local storage medium 17 is deleted.

FIG. 2 is a flowchart showing a flow (from a test to recording in the external storage medium) of each processing executed in the audit log management. Here, for example, it is assumed that a diagnostician conducts a test by utilizing a medical diagnostic device, and an apparatus manager or a service personnel records an audit log file generated at this time in the external recording medium and manages the audit log file, for example.

First, as shown in FIG. 2, in a test using the medical equipment, access to system information or personal information of a patient are constantly accessed for, e.g., activation of the apparatus, registration of a patient name, saving of a test image of a patient, viewing of a test image of a patient or the like. When such an operation is carried out, the application 50 which is a target of this operation in the medical equipment issues each audit log issue event.

The audit log management system 1 accepts the audit log recording request event from the application 50 by using the event accepting section 11, asks the log file generating section 13 for a recording request to generate an audit log at the time of occurrence of each event, and records contents as a temporary file in the apparatus.

The log file generating section 13 generates the temporary file at a predetermined timing, and saves the generated file as an audit log file in the local storage medium 17. This temporary file is saved in the local storage medium 17 at a predetermined timing based on set information stored in the set file section 15 and system information received from the application 50 through the event accepting section 11.

That is, the log file generating section 13 judges whether storage trigger information as a trigger which is set as set information in advance and stores the audit log file in the local storage medium 17 is included in the system information received from the application 50. When the corresponding storage trigger information is included in the system information, the log file generating section 13 executes an operation of saving the temporary file in the local storage medium 17 with reception or detection of the storage trigger information as a trigger.

It is to be noted that the following can be adopted as the storage trigger information.
- A date has been changed.
- A week has been changed.
- A month has been changed.
- The apparatus has entered a standby state.
- The apparatus has entered a pause state.
- The apparatus has been shut down.
- A capacity of the temporary file has exceeded a preset threshold value (a limit value).

Moreover, information used as the storage trigger information can be arbitrarily selected by changing the set information stored in the set file section 15.

Then, the log management section 21 confirms whether the audit log file has been generated (saved) during monitoring of the local storage medium 17. If it is determined that the audit log file has been generated, the log management section 21 issues a compression request to the file compressing section 29 when saving in the local storage medium 17 is completed. The file compressing section 29 executes compression of the audit log file (generates a compressed file in, e.g., a ZIP format), and deletes the compressed original file from the local storage medium 17 when compression of the file is completed.

It is to be noted that, when a test has been repeatedly conducted by utilizing the medical equipment, each processing from acceptance of the audit log recording request to deletion of the compressed original file is repeatedly executed, thereby generating the compressed files for the repeated number times.

Then, the log management section 21 judges how a disk capacity of the local storage medium 17 is reduced by the compressed file from a disk remaining capacity obtained from the local storage medium 17 (or a disk capacity acquiring section 27 which will be described in a second embodiment). For example, the log management section 21 compares a predetermined threshold value with the disk remaining capacity. When the disk remaining capacity is lower than the threshold value, the log management section 21 determines that the disk capacity of the local storage medium 17 is reduced.

If it is determined that the disk capacity of the local storage medium 17 is reduced, the log management section 21 issues a file transfer request to the file transfer section 19. The file transfer section 19 transfers the compressed file stored in the local storage medium 17 to the external medium 31, and deletes the transferred log file in the local storage medium 17 after completion of transfer.

According to the above-described configuration, the following effects can be obtained.

In this audit log management system, the audit log file stored in the local storage medium is compressed at a predetermined timing, and the compressed original file is deleted from the local storage medium. Additionally, a disk remaining capacity of the local storage medium is monitored. If it is determined that the disk capacity is being reduced, the compressed audit log file is transferred from the local storage medium to the external medium, and the transferred compressed audit log file is deleted from the local storage medium. Therefore, a percentage of the compressed audit log file in the overall capacity of the local storage medium can be decreased as much as possible, thereby avoiding a reduction in capacity of the storage medium in the apparatus by storage of the audit log. As a result, inhibition of collection of medical images and a reduction of a test throughput can be avoided, and simplifying transfer of the file to the outside can improve efficiency of an audit log backup operation, thus supporting an improvement in an operation throughput in the hospital.

Further, in this audit log management system, a disk remaining capacity of the local storage medium is monitored. If it is determined that this disk capacity is being reduced, the compressed audit log file is transferred from the local storage medium to the external medium, and the transferred compressed audit log file is deleted from the local storage medium. Therefore, a reduction in capacity of the local storage medium can be always avoided irrespective of whether a file compression ratio is high or low.

Second Embodiment

A second embodiment according to the present invention will now be described. An audit log management system 1 according to this embodiment compresses an audit log file of a local storage medium at a timing different from that in the first embodiment. That is, in the audit log management system 1 according to this embodiment, an operating status of the medical equipment is judged based on information of a test conducted in the medical equipment, a CPU operating status of the medical equipment, a disk capacity of the local storage medium and others, and compression processing of an audit log file is performed at a predetermined timing.

Figure 3:
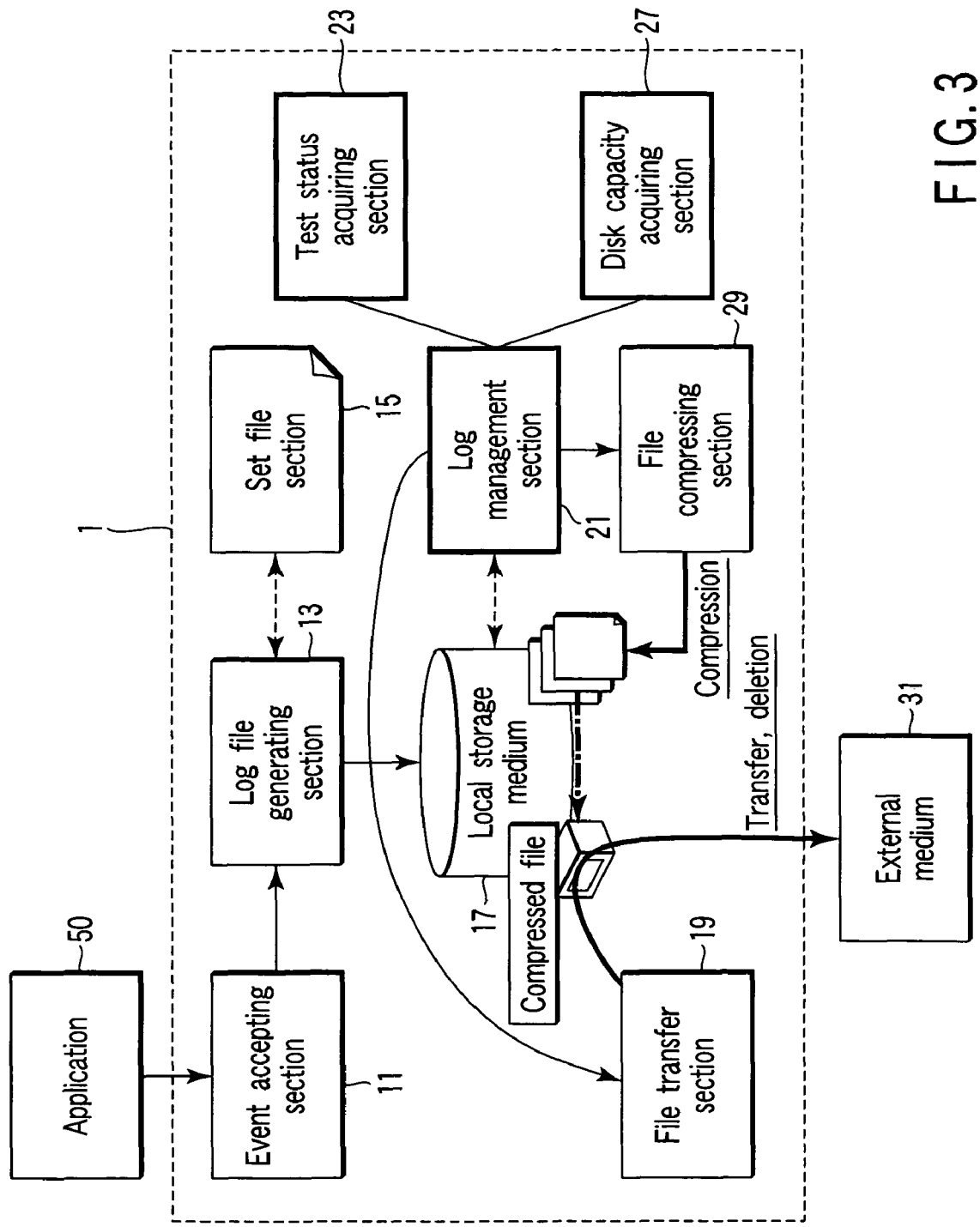
FIG. 3 is a block diagram of a medical equipment according to a second embodiment.

FIG. 3 is a block diagram showing the audit log management system 1 according to the second embodiment. As a difference from the audit log management system according to the first embodiment, the system according to the second embodiment further includes a test status acquiring section 23 and a disk capacity acquiring section 27.

The test status acquiring section 23 acquires/monitors a test status (e.g., start of a test, end of a test, interruption of a test, and restart of a test) using a medical equipment including this audit log management system 1. This monitoring is executed by acquiring an event such as a test start operation or a test end operation of the medical equipment included in system information received from an application 50. Furthermore, the test status acquiring section 23 acquires and monitors a CPU status (e.g., a CPU use ratio) of the medical equipment including this audit log management system 1 as needed based on the system information received from the application 50.

The disk capacity acquiring section 27 acquires/monitors a disk capacity of the local storage medium 17 as needed and judges a disk remaining capacity based on the system information received from the application 50.

Figure 4:
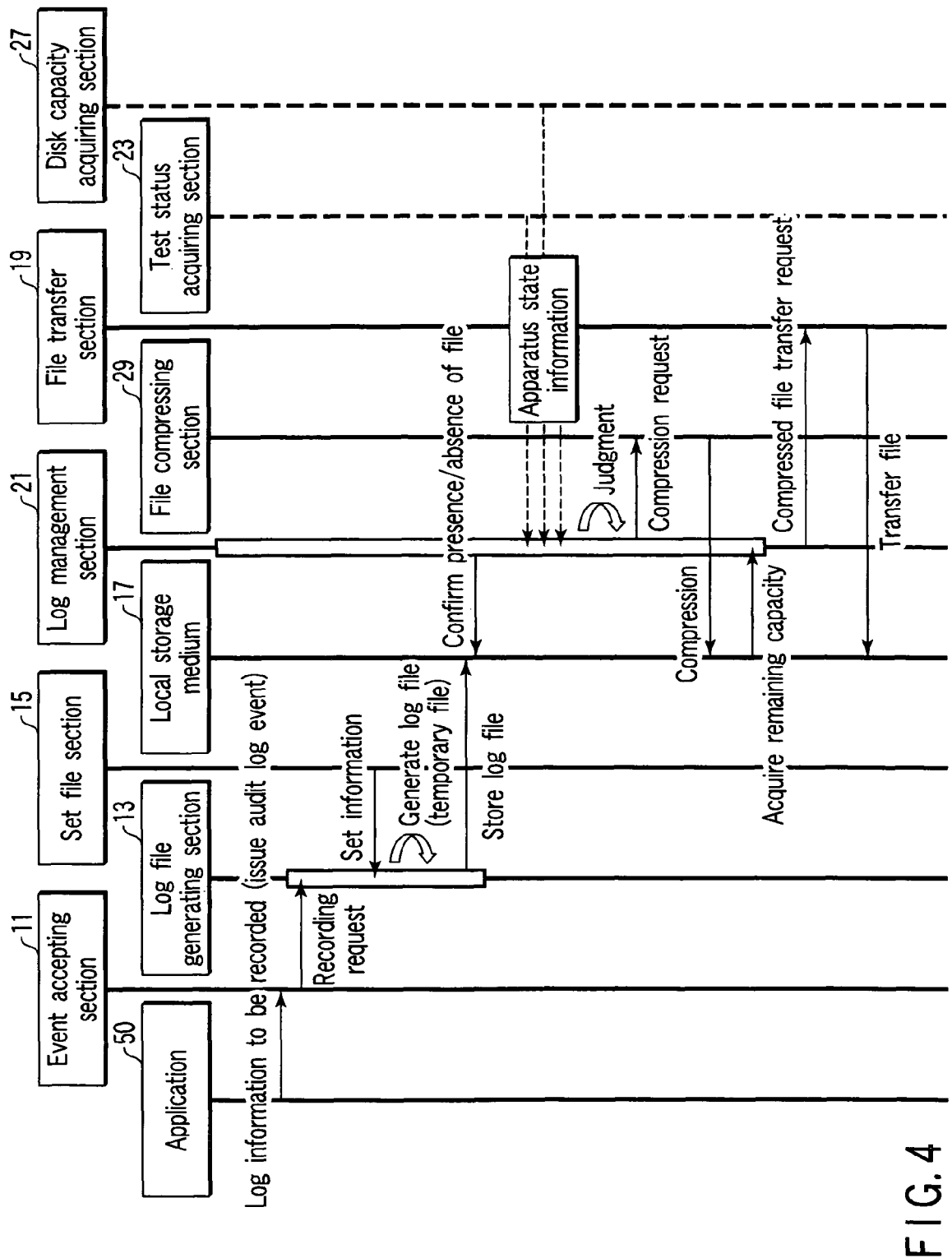
FIG. 4 is a flowchart showing a flow of each processing executed in audit log management in the second embodiment.

FIG. 4 is a flowchart showing a flow of each processing (from a test to recording in an external storage medium) executed in audit log management according to this embodiment. A description will now be given as to an example where compression processing is executed in an idle time (a non-test time) of the medical equipment with reference to this drawing.

In FIG. 4, first, like the first embodiment, there is executed each processing from acceptance of an audit log recording request event from the application 50 to storage of an audit log file in the local storage medium 17.

In this embodiment, a log management section 21 does not immediately issue a compression request to a file compressing section 29 when storage in the local storage medium is completed. The log management section 21 constantly detects/judges a non-test states of the medical equipment or a status which does not obstruct a test with compression start trigger information acquired by the test status acquiring section 23 and the disk capacity acquiring section 27 as a reference. When it is determined that the current status is the status which does not obstruct the test even if compression processing is carried out, the log management section 21 issues a compression request to the file compressing section 29 at this timing. It is to be noted that the following can be adopted as the compression start or stop trigger information, for example.

A test end operation
A test interrupting operation
A CPU use status (a CPU use ratio or the like)
A memory use status (a memory use ratio or the like)
The number of activation processes in the system
A local disk remaining capacity
A status of access to the local disk
The number of audit log files
The number of compressed audit log files
Presence/absence of an audit log file in a compression process When the compression request is supplied to the file compressing section 29 from the log management section 21 based on the above-described judgment, the file compressing section 29 executes compression of a log file in response to this request.

Furthermore, the log management section 21 acquires apparatus information from the test status acquiring section 23 and the disk capacity acquiring section 27 even during the compression processing. When the following compression interruption trigger information is acquired during the compression processing, the log management section 21 transmits a compression stop request to the compressing section to rapidly interrupt the compression processing, and prevents the test itself from being affected by this interruption.

A test has been started.
A test has been restarted.
A use ratio of the CPU has been increased (any application (operation) has been started).
Access to the local disk has been detected.

Figure 5A:
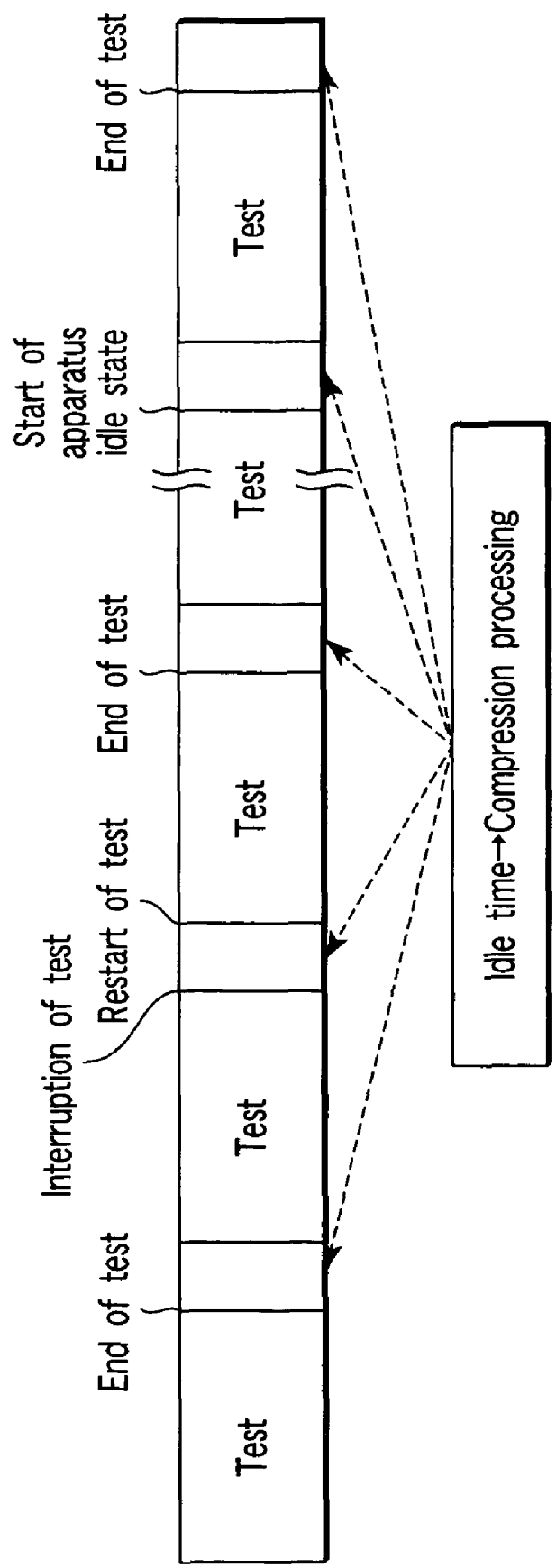
FIG. 5A is a conceptual view showing an example of a compressing operation based on compression interruption trigger information and compression start trigger information.
Figure 5B:
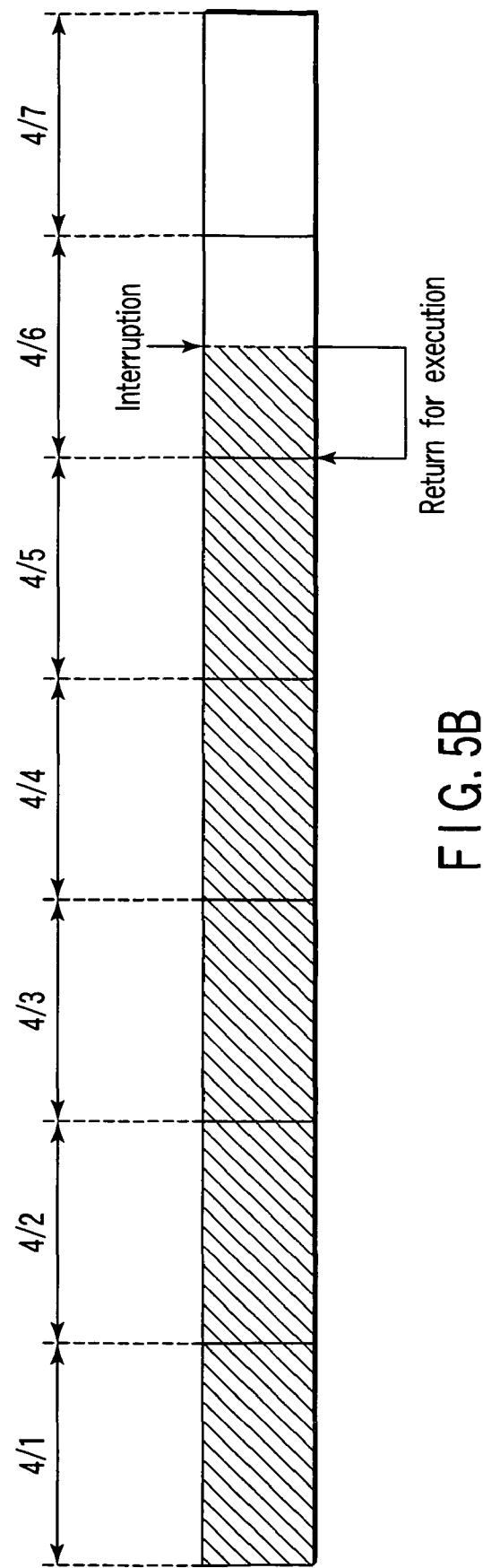
FIG. 5B is a view illustrating restart of compression processing after interruption.

FIG. 5A conceptually shows an example of the compressing operation based on such compression interruption trigger information and compression start trigger information. In this drawing, there is adopted a configuration in which the compression processing of an audit log file is executed during an idle time with respect to a test operation of the medical equipment.

When the compression processing is interrupted in response to a compression stop request from the log management section 21, the file compressing section 29 retraces a predetermined file specified by the log management section 21 to again execute the compression processing. For example, in case of executing the compression processing of audit log files from April 1 to 7, it is assumed that the compression processing of the audit log files from April 1 to 5 has been completed but the compression processing is interrupted in response to the compression stop request during the compression processing of the audit log file of April 6. The log management section 21 monitors an advancing status of the compression processing by the file compressing section 29, and requests the file compressing section 29 to execute the compression processing from the audit log file of April 6 in the next compression processing after interruption. The file compressing section 29 reexecutes the compression processing from the audit log file of April 6 in accordance with this request. It is to be noted that such a restart technique is not restricted to the compression processing, and it is applicable to transfer processing and any other processing which is intended for an audit log and gives a high load to the system.

Then, after the compressing operation is repeatedly executed, the log management section 21 judges how a disk capacity of the local storage medium is reduced by a compressed file from a disk remaining capacity obtained from the disk capacity acquiring section. When the disk capacity reducing status is detected, the log management section 21 issues a file transfer request to a file transfer section 29. The file transfer section 29 transfers a compressed file to an external medium in response to the file transfer request from the log management section 21, and deletes the transferred log file in the local storage medium from the local storage medium after completion of transfer.

According to the above-described configuration, whether the medical equipment is operated can be judged based on information of a test executed in the medical equipment, an operating status of the CPU in the medical equipment, a disk capacity of the local storage medium and others, and the compression processing of an audit log file can be executed at a predetermined timing. Therefore, in addition to the effects described in conjunction with the first embodiment, the compression processing can be executed without lowering performance of the medical equipment as much as possible. As a result, inhibition of collection of medical images and a decrease in test throughput can be avoided, thereby supporting an improvement in an operation throughput in a hospital.

It is to be noted that, when a plurality of audit log files exist, all the audit log files may be compressed based on the same compression start trigger information or the like, or the compression start trigger information or the like may be acquired in accordance with each audit log file so that each audit log file can be compressed based on the acquired information. In any case, it is good enough for the file compressing section 29 to delete the compressed original file from the local storage medium when compression of the file is completed.

Third Embodiment

A third embodiment according to the present invention will now be described. The third embodiment solves a problem which can occur in the second embodiment. That is, in the second embodiment, when a test is conducted in an operating conformation where an idle time is very short, interruption/ restart of the test rarely occurs or an interval between the tests is very short, there can be a case that interruption processing is occasionally generated and compression processing is not completed if a capacity of each audit log file saved in a local storage medium is large. This embodiment sets an audit log file maximum capacity which defines an upper limit of a data size of an audit log file, thereby optimizing a data quantity stored in a local storage medium 17.

A set file section 15 stores a preset audit log file maximum capacity as set information. it is to be noted that this audit log file maximum capacity can be changed to an arbitrary value by a predetermined operation.

A log file generating section 13 generates a log file in accordance with the audit log file maximum capacity stored in the set file section 15. The log file generating section 13 can generate an audit log file having a capacity with which compression processing does not take long time by setting the audit log file maximum capacity to an appropriate value.

The audit log file generated in accordance with the maximum capacity is subjected to compression processing within a short idle time and a short interval between tests in accordance with the procedure described above in conjunction with each of the foregoing embodiments. Further, the compressed audit log file is deleted from the local storage medium.

According to the above-described configuration, a reduction in capacity of the local storage medium due to the audit log can be avoided even in, e.g., an environment where an idle time is very short. As a result, avoiding a reduction in test throughput and simplifying transfer of a file to the outside can realize an increase in efficiency of an audit log backup operation and an improvement in operation throughput in a hospital.

Fourth Embodiment

A fourth embodiment according to the present invention will now be described. This medical equipment can generate information required to verify integrity of an audit log file and verify whether data has been falsified by using the generated information in case of outputting the audit log file to an external storage medium.

Figure 6:
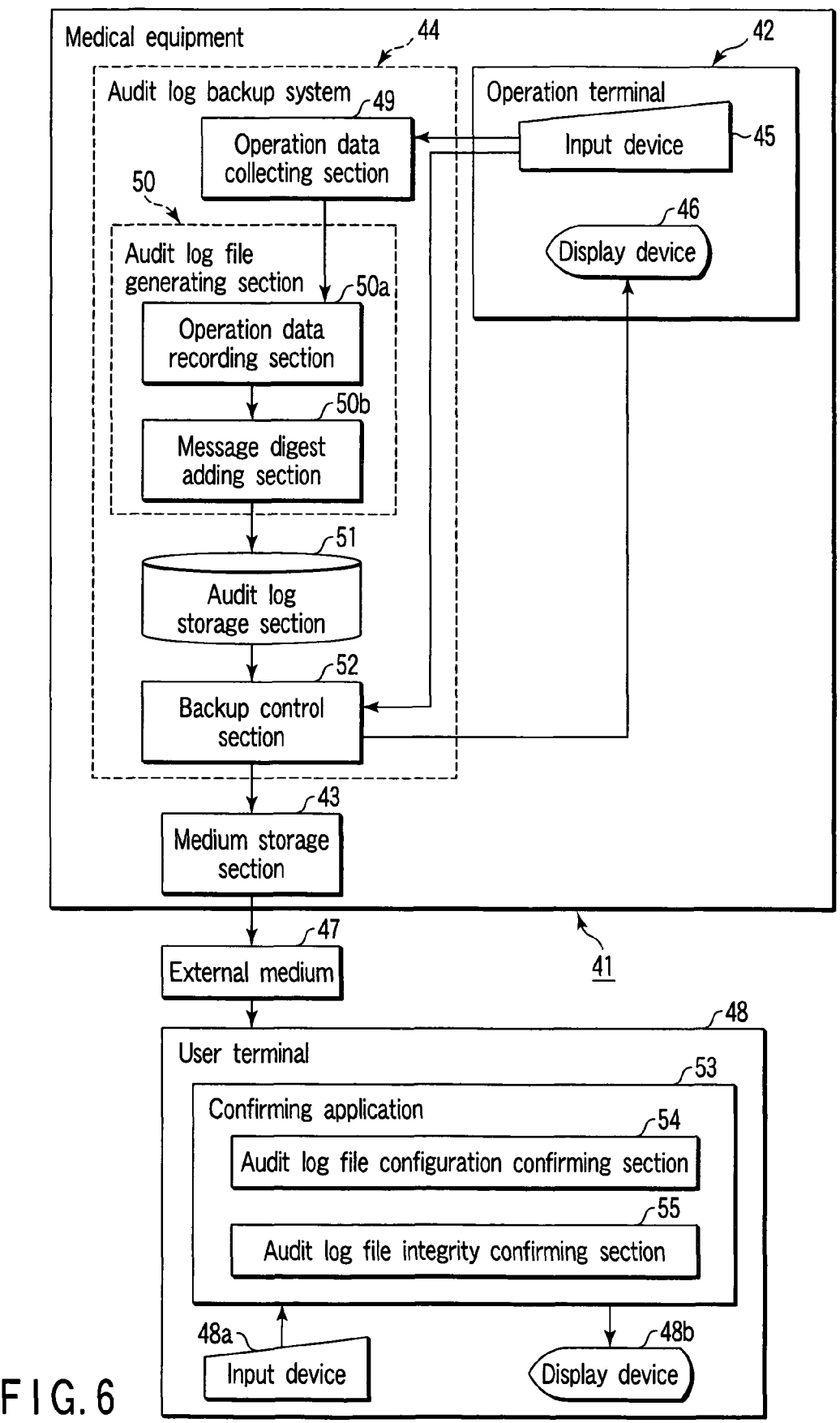
FIG. 6 is a block diagram showing a medical equipment according to a fourth embodiment.

FIG. 6 is a functional block diagram showing an embodiment of a medical equipment according to this embodiment.

A medical equipment 41 is provided with an operation terminal 42 and a medium storage section 43, and has an audit log file output system 44 mounted therein. It is to be noted that an image diagnostic equipment such as an ultrasonic diagnostic equipment, an X-ray CT scanner or an MRI, or a laboratory test apparatus and a medical information system such as HIS, RIS or PACS can be used as the medical equipment 41, and constituent elements required to give functions corresponding to the medical equipment 41 are provided, but they are eliminated here. An input device 45 and a display device 46 which are used to input and operate information are provided in the operation terminal 42.

Furthermore, the medium storage section 43 has a function of outputting information received from the audit log file output system 44 to an external medium 47. The eternal medium 47 is a writable storage medium, and its concrete example is a storage medium such as a USB (Universal Serial Bus) (a registered trademark) memory, an IC (Integrated Circuit) card, a CD (Compact Disk), a DVD (Digital Versatile Disc), an HDD (Hard Disk Drive) or the like. Moreover, information saved in the external medium 47 can be read into the user terminal 48 for reference. As the user terminal 48, it is possible to use a general PC (Personal Computer) as well as an operation terminal of an arbitrary medical equipment.

Although the audit log file output system 44 can be configured by, e.g., allowing a computer to read an audit log file output program, all or a part of the audit log file output system 44 can be configured by using a circuit. Additionally, the audit log file output system 44 is provided with a function of generating an audit log file in the medical equipment 41 and outputting it to the external medium 7. Therefore, the audit log file output system 44 includes an operation data collecting section 49, an audit log file generating section 50, an audit log storage section 51 and a backup control section 52.

The operation data collecting section 49 has a function of collecting operating information of the input device 45 by a user and a function of sequentially giving the collected operating information to the audit log file generating section 50.

The audit log file generating section 50 has a function of generating an audit log file from the operating information of a fixed period or a fixed capacity received from the operation data collecting section 49 and a function of writing and saving the generated audit log file in the audit log storage section 51. For example, a message digest with a fixed length having a characteristic pattern generated from the operating information by an arithmetic operation using a hash function is added to an audit log file in order to verify integrity.

Thus, the audit log file generating section 50 can be configured to include, e.g., an operation data recording section 50a and a message data digest adding section 50b. In this case, the operation data recording section 50a is provided with a function of acquiring operating information from the operation data collecting section 49 and recording the acquired information, and the message digest adding section 50b is provided with a function of reading operating information of a fixed period or a fixed capacity from the operation data recording section 50a and adding a message digest to the read information to create an audit log file.

Not only one message digest is added to one audit log file in which operation data in a given period is collected up, but operation data in one audit log file can be divided into a plurality of units having an arbitrary size, e.g., each single operation data of the input device 45, operation data for one day or operation data for one week, and the message digest can be added to each of such units. As a result, when contents of a part of operation data in an audit log file are falsified, it is possible to specify a timing at which falsification was carried out, and operation data corresponding to a part which is not affected by falsification in the same audit log file can be handled without problem.

However, the audit log file generating section 50 can be configured to create arbitrary audit log integrity verifying information required to verify integrity of an audit log file by using not only means for generating a message digest by utilizing a hash function but also any other equivalent alternative technique such as a check sum or a digital time stamp for confirming integrity of a file when creating an audit log file.

Further, a desired part of an audit log file can be encrypted as required. For example, it is possible to encrypt a body text or hide contents of a part such as time information written in the body text. As a result, a risk of falsification of an audit log file can be reduced.

The audit log storage section 51 has a function of saving an audit log file generated by the audit log file generating section 50 together with audit log integrity verifying information.

The backup control section 52 has a function of supplying a list of audit log files stored in the audit log storage section 51 as list information to the display device 46 where the received information is displayed and, on the other hand, receiving an instruction of an audit log file which should be output to the external medium 47 from the input device 45 when an output request of the audit log file to the external medium 47 is received from the input device 45, and a function of acquiring an audit log file specified by an operation of the input device 45 from the audit log storage section 51 to verify integrity of the audit log file and each operation data based on confirmation of audit log integrity verifying information such as a message digest, and generating integrity verifying information indicating that integrity of the acquired audit log file has been confirmed to be supplied together with the audit log file to the medium storage section 43 when integrity has been confirmed.

On the other hand, when integrity of the audit log file and the operation data has failed to be confirmed based on confirmation of the audit log integrity verifying information such as a message digest, operation data in a corresponding audit log file and a corresponding period and operation can be specified, as described above. For example, when a message digest is sequentially added to each operation data from the input device 45, it is possible to specify which operation data has been falsified. Likewise, when a message digest is sequentially added to operation data for one day, a period in which data has been possibly falsified (in this example, corresponding operation data for one day) can be specified.

Thus, the backup control section 52 can be provided with a function of specifying a corresponding audit log file and a corresponding period and operation when integrity of the audit log file and operation data cannot be confirmed, and a function of supplying to and displaying in the display device 46 information concerning the specified audit log file, period and operation in order to notify a user of this information.

Furthermore, the backup control section 52 can be confirmed in such a manner that a message indicating that "integrity has failed to be confirmed" with respect a part in an audit log file where integrity has not been confirmed is added to the audit log file, or that a file name of an audit log file can be changed to a special file name different from a regular name so that the audit log file whose integrity has not been confirmed can be discriminated from an audit log file whose integrity has been confirmed. That is, the backup control section 52 can be provided with a function of adding information indicating that integrity has not been confirmed with respect to an audit log file whose integrity has not been confirmed.

Moreover, when a message digest is added to an audit log file, after integrity verifying processing of the audit log file, it is possible to use the same or different message digest generated by again applying a hash function using the same or different secrete character string utilized when generating the audit log file, thereby creating integrity verifying information which allows verification of integrity of the audit log file.

As described above, the backup control section 52 has the function of creating the integrity verifying information used to confirm integrity of an audit log file. Additionally, such a backup control section 52 can be mounted in a computer as a backup application which is used to output an audit log file to the external medium 7.

It is to be noted that, when a desired part of an audit log file is encrypted, the backup control section 52 (the backup application) is provided with a function of decrypting the encrypted part.

Here, the integrity verifying information generated by the backup control section 52 can be determined as a confirming application (software) created in a file format. One confirming application is created in common when a plurality of audit log files are output to a single external medium 47, and various kinds of functions required to confirm integrity of each audit log file can be provided to the confirming application. For example, when a confirming application 53 is read into the user terminal 48, the user terminal 48 can be allowed to function as an audit log file configuration confirming section 54 and an audit log file integrity confirming section 55. However, it is determined that the user terminal 48 includes an input device 48a and a display device 48b like the medical equipment 41 and is provided with a function corresponding to the operation terminal 42 of the medical equipment 41.

In this case, the audit log file configuration confirming section 54 judges whether a file configuration of an audit log file stored in the same external medium 47 is complete. The audit log file configuration confirming section 54 has a function of creating information notifying a user of the fact that the file configuration is not complete if it is determined that the file configuration is not complete. The audit log file integrity confirming section 55 has a function of verifying integrity of an audit log file stored in the same external medium 47 based on confirmation of a message digest and creating information notifying a user of the audit log file whose integrity has not been confirmed.

It is to be noted that, when a desired part of an audit log file is encrypted, the confirming application 53 (the audit log file integrity confirming section 55) is provided with a function of decrypting the encrypted part to confirm integrity or displaying a body text.

Therefore, an audit log file and integrity verifying information supplied from the backup control section 52 can be output from the medium storage section 43 to the external medium 47.

A function of the medical equipment 41 will now be described.

FIG. 7 is a flowchart showing a flow of generating an audit log in the medical equipment 1 depicted in FIG. 6 and outputting the generated audit log to the external medium 47, and each reference symbol having S and a number in the drawing denotes each step in the flowchart.

First, at a step S1, when a user operates the input device 45 to manipulate the medical equipment 1, the operation data collecting section 49 collects operation information and sequentially supplies it to the audit log file generating section 50.

Then, at a step S2, the audit log file generating section 50 generates an audit log file from each operation information of a fixed period or a fixed capacity received from the operation data collecting section 49, and writes and stores the generated audit log file in the audit log storage section 51. Therefore, audit log files generated in the audit log file generating section 50 are classified in accordance with each fixed period or each fixed capacity and saved in the audit log storage section 51.

Figure 8:
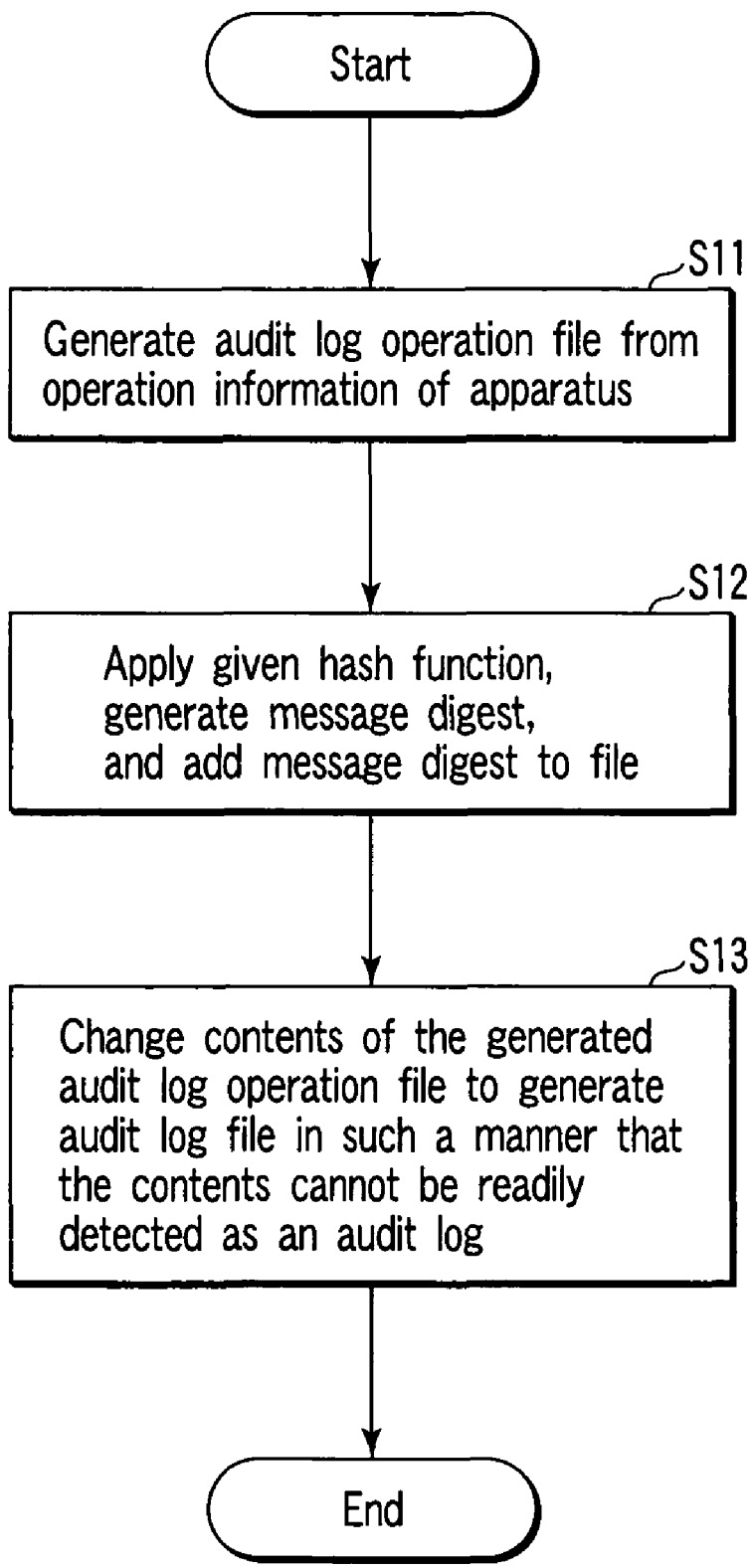
FIG. 8 is a flowchart showing an example of a detailed procedure when generating an audit log file by an audit log file generating section of the medical equipment depicted in FIG. 6.

FIG. 8 is a flowchart showing an example of a detailed procedure when generating an audit log file by the audit log file generating section 50 in the medical equipment 41 depicted in FIG. 6, and each reference symbol having S and a number in the drawing denotes each step in the flowchart.

First, at a step S11, the audit log file generating section 50 generates an audit log operation file, divides time-series operating information sequentially received from the operation data collecting section 49 in accordance with each fixed period or capacity, and writes such information in the generated audit log operation file.

Then, at a step S12, the audit log file generating section 50 adds information required to confirm integrity of data to the audit log operation file. Specifically, a hash code is generated in the form of a given secret character string with respect to contents of the audit log operation file, and added to a body text of the operating information. That is, a message digest is generated by applying a given hash function, and added to the audit log operation file as audit log integrity verifying information.

Then, at a step S13, the audit log file generating section 50 changes an extension to generate an audit log file in such a manner that contents of the created audit log operation file cannot be readily detected as an audit log. At this time, a body text of the audit log file is encrypted as required.

Further, the thus generated audit log file is written and stored in the audit log storage section 51. Furthermore, a user can activate the backup application to store in the external medium 47 the audit log file saved in the audit log storage section 51.

That is, at a step S3 in FIG. 7, when the backup application is activated, the backup control section 52 verifies integrity of an audit log file specified by the input device 45, and supplies the audit log file together with the confirming application 53 to the medium storage section 43 when integrity is confirmed.

Figure 9:
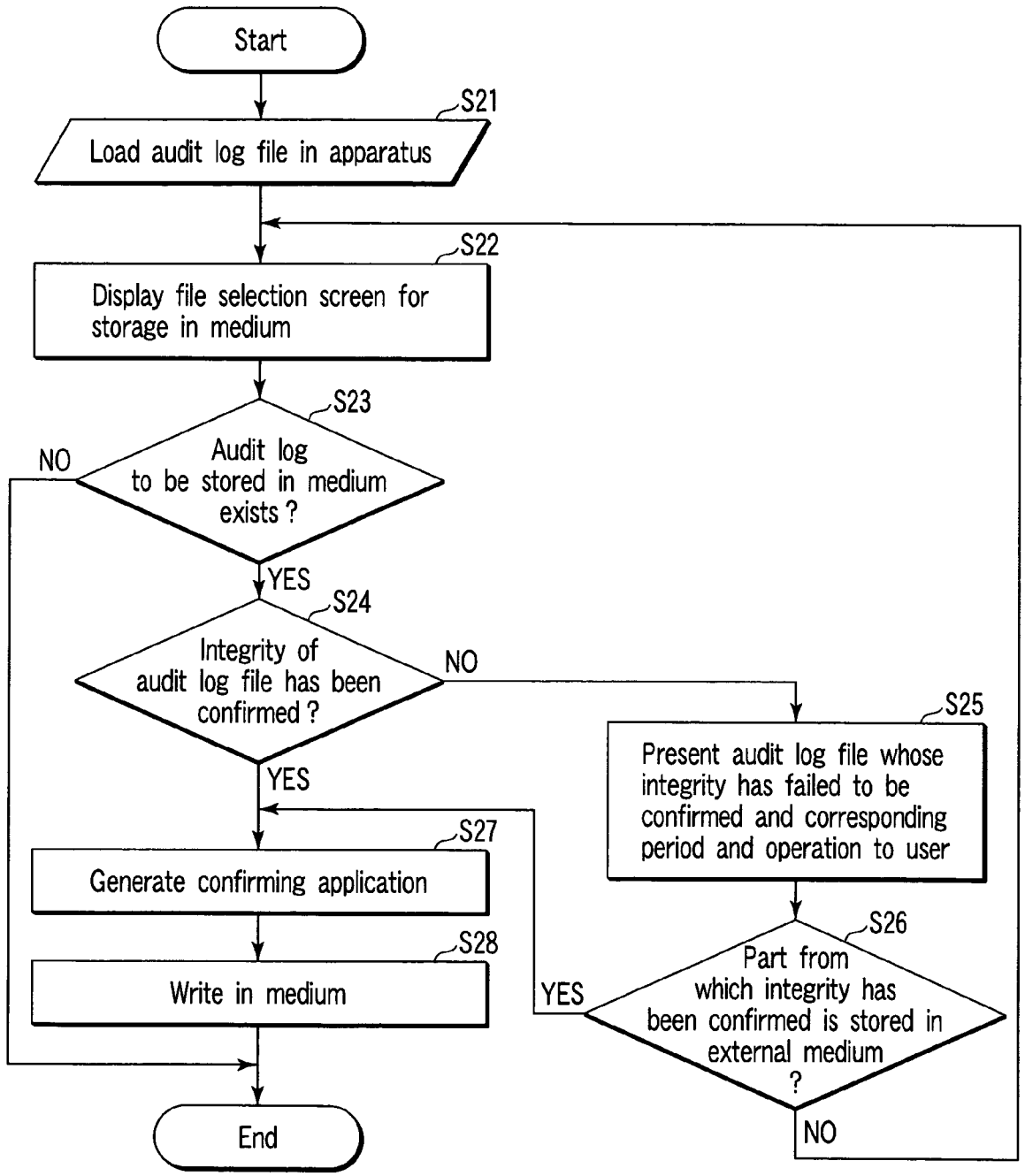
FIG. 9 is a flowchart showing an example of a detailed procedure when integrity of an audit log file is confirmed by a backup control section of the medical equipment depicted in FIG. 6 and the audit log file is output to an external medium together with a confirming application.

FIG. 9 is a flowchart showing an example of a detailed procedure when confirming integrity of an audit log file by the backup control section 52 in the medical equipment 41 depicted in FIG. 6 and outputting the audit log file together with the confirming application 53 to the external medium 7, and each reference symbol having S and a number in the drawing denotes each step in the flowchart.

First, at a step S21, upon receiving an output request of an audit log file to the external medium 7 from the input device 45, the backup control section 52 loads audit log files from the audit log storage section 51.

Then, at a step S22, the backup control section 52 supplies a list of audit log files loaded from the audit log storage section 51 as list information to the display device 46 where the list information in displayed. Therefore, the display device 46 displays a screen for selecting the audit log file which should be stored in the external medium 47.

Subsequently, at a step S23, the backup control section 52 judges presence/absence of an instruction of the audit log file which should be stored in the external medium 47. Furthermore, when the instruction of the audit log file which should be stored in the external medium 47 is not input from the input device 45, the processing is terminated.

When a user selects the audit log file to be stored in the external medium 47 from the input device 45 and the instruction of the audit log file to be stored in the external medium 47 is given to the backup control section 52, the backup control section 52 confirms a message digest with respect to each selected audit log file to confirm integrity of information and then judges whether integrity of all the selected audit log files has been confirmed at a step S24.

Moreover, if there are audit log files whose integrity has not been confirmed, the backup control section 52 supplies a list of the audit log files whose integrity has not been confirmed to the display device 46 at a step S25. Additionally, the backup control section 52 specifies a period or a operation, from which integrity has failed to be confirmed, of operation data recorded in each audit log file whose integrity has not been confirmed, and supplies an obtained result to the display device 46, thereby informing a user.

At this time, a message indicating that "integrity has not been confirmed" with respect to a part from which integrity has failed to be confirmed is added to the audit log file.

Then, at a step S26, the backup control section 52 supplied screen information to the display device 46 where the supplied information is displayed. The screen information allows a user to select whether the audit log file whose integrity has not been confirmed is to be output to the external medium 47. Further, the user can select and instruct whether the audit log file can be stored by an operation of the input device 45. Furthermore, upon receiving operating information from the input device 45, the backup control section 52 judges whether a part of the audit log file from which integrity has been confirmed is to be stored in the external medium 47.

Moreover, when a user does not want to store the part of the audit log file from which integrity has been confirmed in the external medium 47, the audit log file selection screen is again displayed in the display device 46 at the step S22, and the backup control section 52 waits for a selecting instruction from the input device 45.

On the other hand, when it is determined that the part of the audit log file from which integrity has been confirmed is to be stored in the external medium 47 at the step S26, or when it is determined that there is no audit log file whose integrity has not been confirmed at the step S24, the backup control section 52 generates the confirming application required to confirm integrity of audit log files at a step S27. This confirming application 53 confirms the hash code used when the audit log file generating section 50 generates an audit log file, and can be generated by using the same character string as the secrete character string used when creating the audit log file.

Then, at a step S28, the backup control section 52 supplies each audit log file whose integrity has been confirmed together with the confirming application 53 to the medium storage section 43. Therefore, the medium storage section 43 stores each audit log file and the confirming application 53 fed from the backup control section 52 in the external medium 47. That is, each audit log file and the confirming application 53 are written in the external medium 47 from the medium storage section 43.

It is to be noted that each audit log file stored in one given external medium 7 is generated by using the common hash function, and hence one confirming application 53 for confirmation of integrity of each audit log file is generated in common with respect to one medium. In other words, in case of saving a plurality of audit log files in the single external medium 47, the hash function must be shared, and one confirming application 53 is generated with respect to one medium.

Moreover, a user stores an audit log file for, e.g., backup in the external medium 47, and hence can make reference to the audit log file stored in the external medium 47 at a desired timing.

In case of making reference to an audit log file from the external medium 47, at a step S4 in FIG. 7, the audit log file and the confirming application 53 stored in the external medium 47 are read into the user terminal 48. Additionally, the confirming application 53 is activated in the user terminal 48.

FIG. 10 is a flowchart showing an example of a detailed procedure of activating the confirming application 53 input from the external medium 47 to make reference to an audit log file, and each reference symbol having S and a number in the drawing denotes each step in the flowchart.

First, at a step S31, the confirming application 53 stored in the external medium 7 is activated in the user terminal 48. Then, the user terminal 48 functions as the audit log file configuration confirming section 54 and the audit log file integrity confirming section 55.

Subsequently, at a step S32, a file configuration of an audit log file in the external medium 47 is confirmed by the audit log file configuration confirming section 54. That is, the audit log file configuration confirming section 54 judges whether the file configuration of the audit log file stored in the same external medium 47 is complete, i.e., whether an audit log file is missing.

Further, if it is determined that the file configuration of the audit log file is not complete, the audit log file configuration confirming section 54 generates information notifying a user of the fact that the file configuration is not complete and displays this information in a screen of the user terminal 48 at a step S33.

Furthermore, if it is not determined that the file configuration of the audit log file is incomplete, or after the information indicating that the file configuration of the audit log file is incomplete is displayed, the user terminal 48 waits for selection of an audit log file to which reference should be made.

Then, at a step S34, when information of selection of an audit log file to which reference should be made is accepted by an operation of the user terminal 48, the audit log file integrity confirming section 55 loads the selected audit log file from the external medium 47.

Subsequently, at a step S35, the audit log file integrity confirming section 55 verifies integrity of the reference target audit log file loaded from the external medium 47 by confirming a message digest, and judges whether integrity of the audit log file has been confirmed.

Moreover, when integrity of the audit log file has not been confirmed, the audit log file integrity confirming section 55 creates information notifying a user of the audit log file whose integrity has not been confirmed at a step S36. Therefore, the audit log file whose integrity has not been confirmed is displayed in the screen of the user terminal 48, and the user terminal 48 waits for selection of an audit log file which should be referred.

On the other hand, when integrity of the audit log file has been confirmed, the selected audit log file is displayed in the screen of the user terminal 48 at a step S37.

A user can confirm the number of audit log files stored in the external medium 47 to verify whether a file configuration of each audit log file is complete through the user terminal 48 by using such a confirming application 53. Further, it is possible to confirm a message digest with respect to each audit log file in the external medium 47, and determine that the audit log file which has failed to be confirmed has been destroyed or falsified.

FIG. 11 is a conceptual view showing an entire flow from generation of an audit log file in the medical equipment 1 depicted in FIG. 6 to reference to the audit log file through the external medium 7.

In the medical equipment 41, the audit log file generating section 50 generates an audit log operation file from operation data, and creates a hash code by using a log file generating function (a hash function). As a result, there is produced an audit log file having a digest message added to the operation data which is a body text.

Furthermore, the audit log file is stored in the audit log storage section 51 in the medical equipment 41. However, when a user activates the backup application by operating the operation terminal 42 to select an audit log file which is to be backed up in the external medium 47, a digest message of each selected audit log file is confirmed by the backup control section 52 (the backup application) to verify integrity of each audit log file.

Then, the backup application generates the confirming application 53 for checking a hash code shared by respective audit log files whose integrity has been confirmed, and output the generated confirming application 53 together with each audit log file to the external medium 47.

Therefore, the external medium 47 stores one or more audit log files each consisting of a body text and a digest message and one confirming application 53 for checking the hash code. Further, the user operates the user terminal 48 to activate the confirming application 53 stored in the external medium 47 so that he/she can verify integrity of each audit log file and thereby make reference.

That is, in case of outputting an audit log file, the above-described medical equipment 41 confirms integrity of the audit log file and then generates the confirming application 53 for integrity, whereby the confirming application 53 is stored together with the audit log file as an integrity confirmation target in the external medium 47.

Therefore, according to the medical equipment 41, even in case of making reference to an audit log file stored in the external medium after a given fixed period, the confirming application 53 stored in the same external medium 47 can be used to verify whether the externally output audit log file is being stored in the medical equipment 41. That is, it is possible to confirm whether information has been destroyed or falsified in a period from storage of the audit log file in the external medium 41 to reference to the audit log file.

Furthermore, even if a plurality of audit log files are stored in the external medium 47, the number of confirming application 53 stored in the external medium 47 is one, and integrity of all the audit log files in the external medium 47 is confirmed by the common confirming application 53. Therefore, it is possible to not only verify integrity of each audit log file but also confirm a file configuration of each audit log file (the number of files) stored in the external medium 47.

Fifth Embodiment

A fifth embodiment according to the present invention will now be described. An audit log management system according to this embodiment verifies whether data has been falsified by using information required to verify integrity of an audit log file described in the fourth embodiment in the audit log management system according to the first embodiment.

Figure 12:
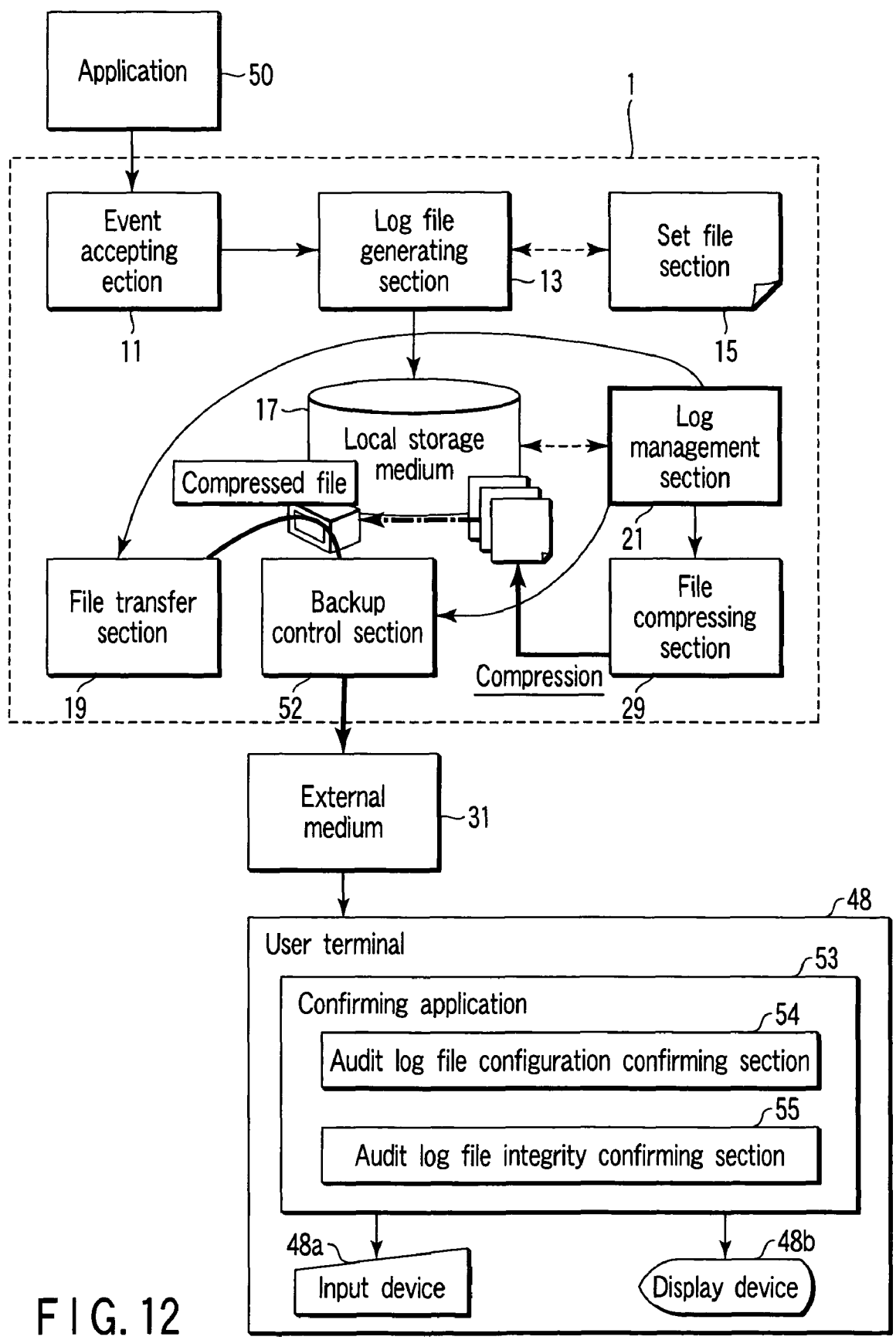
FIG. 12 is a view showing an audit log management system and a user terminal according to a fifth embodiment.

FIG. 12 is a view showing an audit log management system and a user terminal according to this embodiment. This embodiment is mainly different from the audit log management system depicted in FIG. 1 in that an event accepting section 11, a log file generating section 13, a function of a local storage medium 17 and a backup control section 52 are further provided.

The event accepting section 11 is provided with a function of the operation data collecting section 49 depicted in FIG. 6; the log file generating section 13, a function of the audit log file generating section 50 depicted in FIG. 6; and the local storage medium 17, a function of the audit log storage section 51 shown in FIG. 6, respectively. Moreover, a function of the backup control section 52 is as described above.

Figure 13:
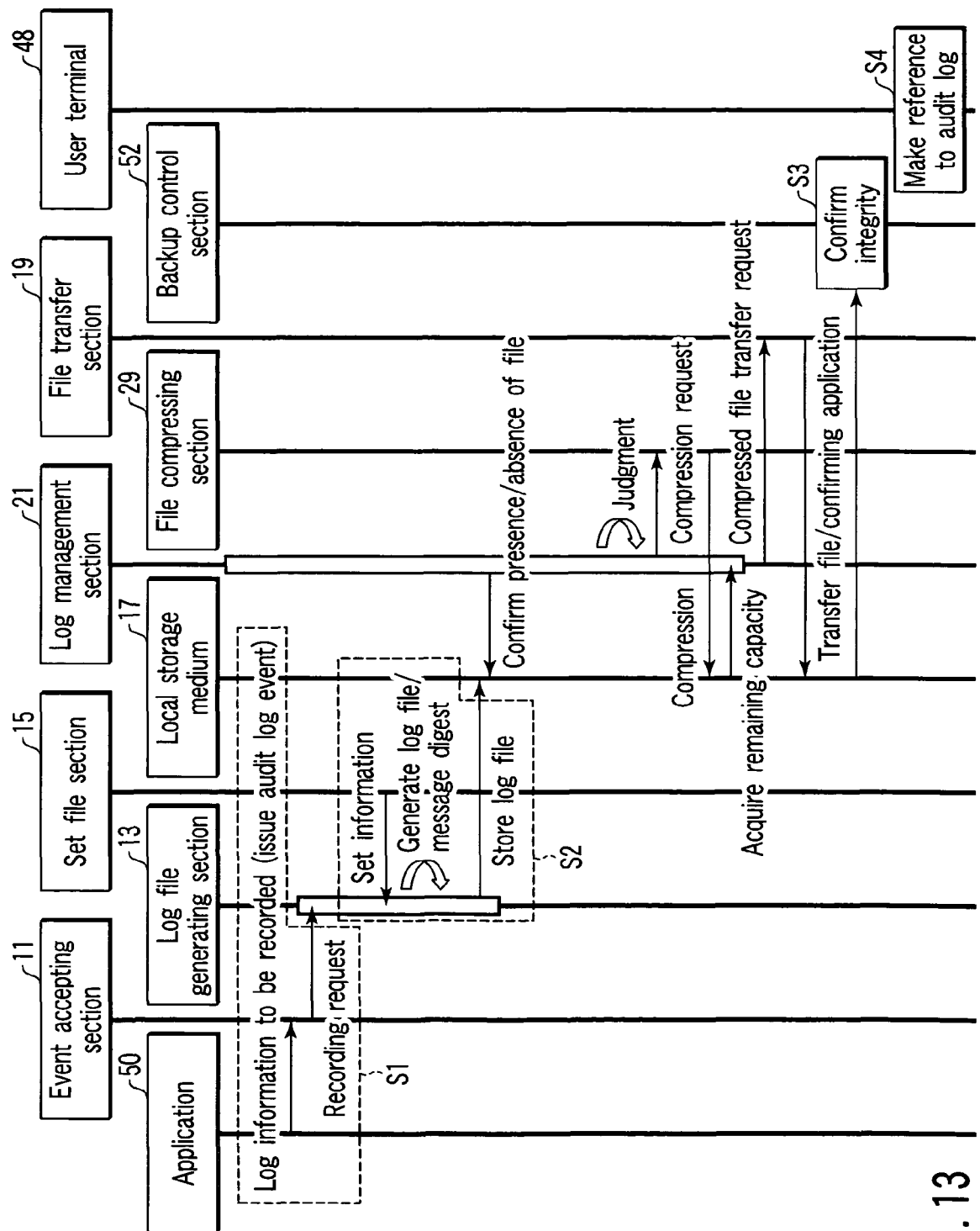
FIG. 13 is a flowchart showing a flow of each processing executed in audit log management according to the fifth embodiment.

FIG. 13 is a flowchart showing a flow of each processing (from a test to reference of an audit log file in a user terminal 48) executed in the audit log management according to this embodiment. First, as shown in FIG. 13, when a predetermined operation is carried out in a test using a medical equipment, an application 50 intended for this operation in the medical equipment issues each audit log issue event. An audit log management system 1 accepts an audit log recording request event from the application 50 by the event accepting section 11 (corresponding to the step S1 in FIG. 7).

The log file generating section 13 generates an audit log at the time of occurrence of each event and information used to confirm integrity of data (e.g., a message digest) in response to the recording request from the event accepting section 11, and records contests as a temporary file in the apparatus. Further, the log file generating section 13 creates a temporary file at a predetermined timing, and saves it as an audit log file in the local storage medium 17. This temporary file is stored in the local storage medium 17 at a predetermined timing (e.g., with storage trigger information being used as a reference) based on set information stored in a set file section 15 and system information received from the application 50 through the event accepting section 11 (corresponding to the step S2 in FIG. 7 and the steps S11 to S13 in FIG. 8).

Then, a log management section 21 confirms whether an audit log file has been created (or stored) during monitoring of the local storage medium 17. If it is determined that the audit log file has been created, the log management section 21 issues a compression request to a file compressing section 29 when storage in the local storage medium 17 is completed. The file compressing section 29 executes compression of the audit log file (generates a compressed file in, e.g., a ZIP format), and deletes the compressed original file from the local storage medium 17 when compression of the file is completed.

It is to be noted that, when a test has been repeatedly conducted by utilizing the medical equipment, each processing from acceptance of the audit log recording request event to deletion of the compressed original file is repeatedly executed, whereby the compressed file is created for the repeated number of times.

Then, the log management section 21 judges how a disk capacity of the local storage medium 17 is reduced by the compressed file from a disk remaining capacity obtained from the local storage medium 17 (or a capacity acquiring section 27). For example, the log management section 21 compares a predetermined threshold value with the disk remaining capacity. If the disk remaining capacity is lower than the threshold value, the log management section 21 determines that the disk capacity of the local storage medium 17 is being reduced. When it is determined that the disk capacity of the local storage medium 17 is being reduced, the log management section 21 issues a file transfer request to a file transfer section 19.

The file transfer section 19 transfers the compressed file stored in the local storage medium 17 to the backup control section 52, and deletes the transferred log file in the local storage medium 17 after completion of transfer. The backup control section 52 confirms integrity of the audit log file by executing each processing from the step S24 to the step S28 shown in FIG. 9, and supplies a confirming application 13 together with the audit log file to an external medium 31.

In the user terminal 48, in case of making reference to an audit log file, the confirming application 13 input from the external medium 31 is activated, and each processing shown in FIG. 10 is thereby executed.

According to the above-described configuration, a percentage of a compressed audit log file in an overall capacity of the local storage medium can be reduced as much as possible, and whether information has been destroyed or falsified can be confirmed in a period from storage of an audit log file in the external medium to reference. Therefore, it is possible to avoid inhibition of a medical image collecting operation and a reduction in test throughput due to processing intended for an audit log file, e.g., compression or transfer, and safety of information of audit log file can be secured.

Sixth Embodiment

A sixth embodiment according to the present invention will now be described. An audit log management system according to this embodiment verifies whether data has been falsified by using information used to verify integrity of the audit log file described in the fourth embodiment in the audit log management system according to the second embodiment.

Figure 14:
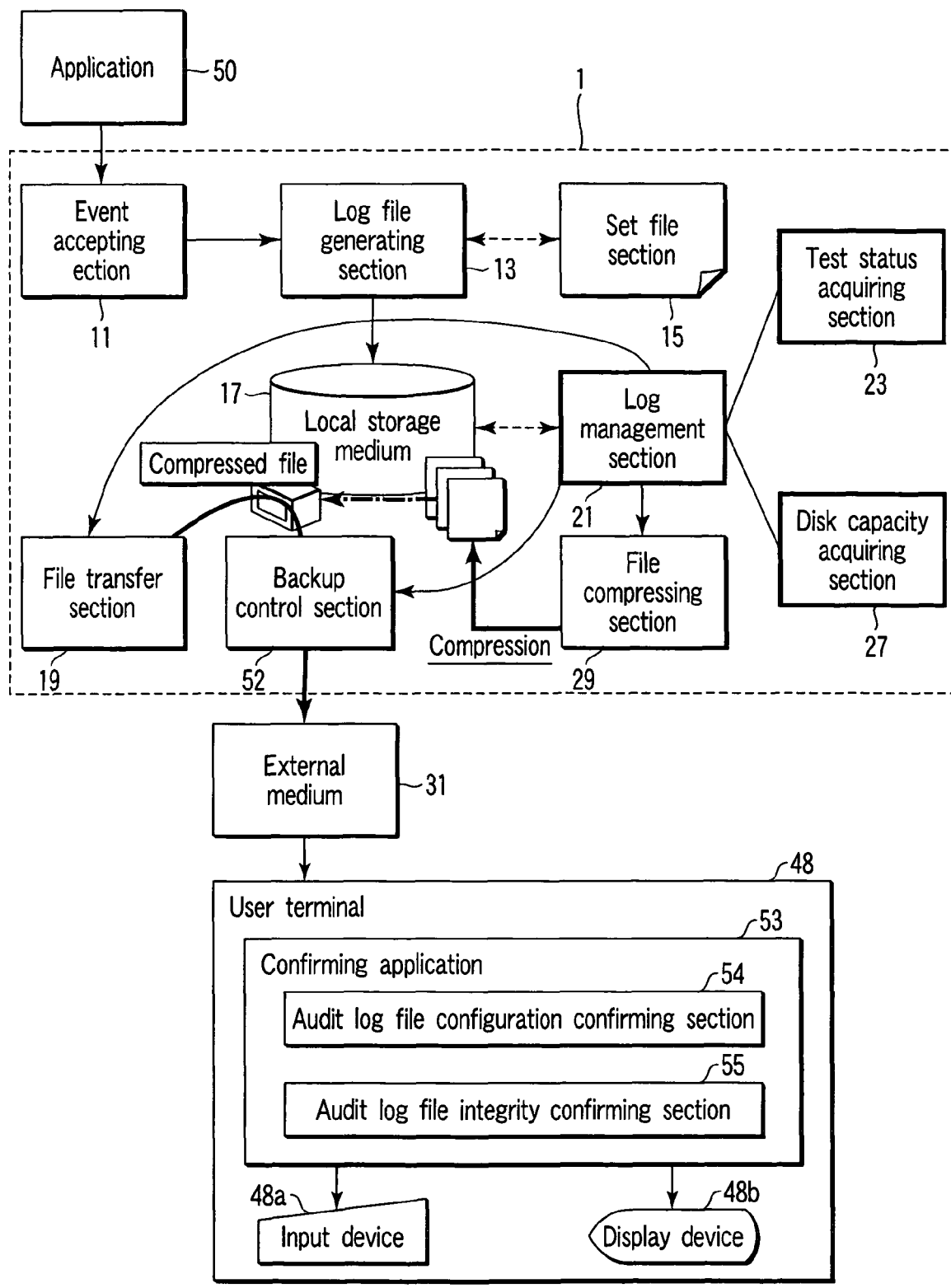
FIG. 14 is a view showing an audit log management system and a user terminal according to a sixth embodiment.

FIG. 14 is a view showing an audit log management system and a user terminal according to this embodiment. This embodiment is mainly different from the audit log management system shown in FIG. 3 in that an event accepting section 11, a log file generating section 13, a function of a local storage medium 17 and a backup control section 52 are further provided.

The event accepting section 11 is provided a function of the operation data collecting section 49 depicted in FIG. 6; the log file generating section 13, a function of the audit log file generating section 50 depicted in FIG. 6; and the local storage medium 17, a function of the audit log storage section 51 shown in FIG. 6, respectively. Further, a function of the backup control section 52 is as described above.

FIG. 15 is a flowchart showing a flow of each processing (from a test to reference of an audit log file on the user terminal 48) executed in the audit log management according to this embodiment. As shown in the drawing, first, like the fifth embodiment, there is executed each processing from acceptance of an audit log recording request event from an application 50 to storage of an audit log file and information used to verify integrity of the audit log file (e.g., a message digest) in the local storage medium 17.

Then, a log management section 21 constantly detects/judges a non-test status of a medical equipment or a status which does not obstruct a test with compression start trigger information acquired by a test status acquiring section 23 and a disk capacity acquiring section 27 being used as a reference. When it is determined that the current status is a status that a test is not obstructed even if compression processing is executed, the log management section 21 issues a compression request to a file compressing section 29 at this timing.

When the compression request from the log management section 21 is supplied to the file compressing section 29 based on the above-described judgment, the file compressing section 29 executes compression of a log file in response to this request.

Furthermore, the log management section 21 acquires apparatus information from the test status acquiring section 23 and the disk capacity acquiring section 27 even during compression processing. For example, if already indicated compression interruption trigger information is acquired during the compression processing, the log management section 21 transmits a compression stop request to the compressing section to rapidly interrupt the compression processing, and operates in such a manner that the test itself is not affected.

Then, after the compressing operation is repeatedly executed, the log management section 21 judges how a disk capacity of a local storage medium is reduced by a compressed file from a disk remaining capacity obtained from the disk capacity acquiring section. When a disk capacity reducing status is detected, the log management section 21 issues a file transfer request to a file transfer section 29. The file transfer section 29 transfers the compressed file to an external medium in response to the file transfer request from the log management section 21, and deletes the transferred log file in the local storage medium from the local storage medium after completion of transfer. Thereafter, like the fifth embodiment, processing of confirming integrity of an audit log file, processing of making reference to an audit log file in the user terminal 48 and others are executed.

According to the above-described configuration, in addition to the effects mentioned in the fifth embodiment, processing intended for an audit log file such as compression or transfer can be executed without lowering performance of the medical equipment as much as possible.

It is to be noted that, besides the configuration of this embodiment, a data quantity stored in the local storage medium 17 may be optimized by setting an audit log file maximum capacity which defines an upper limit of a data size of an audit log file like the third embodiment.

The present invention is not restricted to the foregoing embodiments, and constituent elements can be modified without departing from the scope of the invention on embodying stages, thereby embodying the present invention. As a concrete modification, there are the following examples.

(1) Each function according to this embodiment can be likewise realized by installing a program executing the processing in a computer such as a workstation and developing such a program in a memory. At this time, a program which can allow the computer to execute this technique can be stored in a storage medium such as a magnetic disk (a floppy (a registered trademark) disk, a hard disk or the like), an optical disk (a CD-ROM, a DVD or the like) or a semiconductor memory for distribution.

(2) In the second embodiment, compression processing of an audit log file is executed in accordance with an operation status of the medical equipment. On the other hand, a dedicated button used to instruct compression processing may be provided to a non-illustrated operating section, a GUI of a device screen or the like and this button may be manually operated so that a user can execute compression processing at an arbitrary timing.

(3) In each of the foregoing embodiments, patient information is constituted of diagnostic information and collateral information including at least a patient name (or a patient ID) and a test type. However, the present invention is not restricted thereto, and the patient information may take any configuration as long as it includes information which can directly specify a patient (e.g., a patient name, a patient ID or the like) or information which can indirectly specify a patient (e.g., a diagnostic image, a test result, a treatment history, a weight, a height, a gender, preferences and others).

(4) In each of the foregoing embodiments, the description has been given on the example where an execution timing of compression and transfer processing of an audit log file which substantially gives a high load to a system is controlled based on an operating state of the medical equipment. However, the present invention is not restricted to this example, and an execution timing of encryption processing of an audit log file, processing of adding information used to confirm integrity to an audit log file, processing of confirming integrity of an audit log file and others may be controlled based on an operating state of the medical equipment. In such a case, it is good enough for the backup control section 52 to execute the encryption processing of an audit log file, the processing of confirming integrity of an audit log file and others in response to a request from the log management section 21. Furthermore, for example, when the processing of adding information used to confirm integrity to each audit log file is performed in the backup control section 52 after generating a fixed quantity of audit log files, a high load is given to the system. In such a case, it can be said that practical benefits of controlling an execution timing of this processing based on an operating state of the medical equipment are particularly high.

Moreover, various inventions can be formed by appropriately combining a plurality of constituent elements disclosed in the foregoing embodiments. For example, some constituent elements may be eliminated from all constituent elements disclosed in the embodiments. Additionally, constituent elements in different embodiments may be appropriately combined.

What is claimed is:

1. A medical equipment comprising:
a log generating unit which generates a log concerning an operation dealing with patient information and an operation of the medical equipment, the log including an information of an operator that operates the medical equipment, a time of the operation of the medical equipment, and content of the operation of the medical equipment; and
a log management unit which determines an execution timing of log target processing as processing which uses the log and substantially gives a high load to the medical equipment based on an operation state of the medical equipment, and executes the log target processing at the determined timing, wherein the log target processing includes compression processing of compressing the log concerning the operation dealing with patient information and the operation of the medical equipment to generate a compressed log;
a storage unit which stores the compressed log generated by the log generating unit, and
wherein the log management unit determines the execution timing of the log target processing based on one of:
interruption of a diagnostic operation,
termination of a diagnostic operation,
CPU operating status,
CPU use ratio,
memory use status,
memory use ratio,
a number of activation processes in the system,
a local disk remaining capacity,
a status of access to the local disk,
a number of audit log files,
a number of compressed audit log files,
presence/absence of an audit log file in a compression process,
a date has been changed,
a week has been changed,
a month has been changed,
the apparatus has entered a standby state,
the apparatus has entered a pause state,
the apparatus has been shut down.

2. The medical equipment according to claim 1, wherein the patient information includes diagnostic information concerning a patient and collateral information including at least a patient name and a type of a test conducted to the patient.

3. The medical equipment according to claim 1, wherein the log management unit determines the execution timing of the log target processing in such a manner that the log target processing is started when the medical equipment interrupts or terminates a diagnostic operation.

4. The medical equipment according to claim 1, wherein the log management unit determines the execution timing of the log target processing in such a manner that the log target processing is interrupted or terminated when the medical equipment starts a diagnostic operation.

5. The medical equipment according to 1, wherein the log target processing includes transfer processing of transferring the compressed log to an external storage device.

6. The medical equipment according to claim 1,
wherein the log management unit determines an execution timing of the compression processing based on an operation state of the medical equipment, and
the log management unit executes the compression processing and deletes a log as a target of the compression processing from the storage unit with the determined execution timing of the compression processing being used as a reference.

7. The medical equipment according to claim 1, wherein the log management unit determines an execution timing of the compression processing based on a capacity reducing state of the storage unit, and the log management unit executes the compression processing and deletes a log as a target of the compression processing from the storage unit with the determined execution timing of the compression processing being used as a reference.

8. The medical equipment according to claim 1, further comprising an instruction unit which instructs the log management unit to execute the compression processing, wherein the log management unit executes the compression processing and deletes a log as a target of the compression processing from the storage unit in response to an instruction from the instruction unit.

9. The medical equipment according to claim 5, wherein the log management unit determines an execution timing of the transfer processing based on a capacity reducing state of the storage unit, and the log management unit executes the transfer processing and deletes a log as a target of the compression processing from the storage unit with the determined execution timing of the transfer processing being used as a reference.

10. The medical equipment according to claim 1, wherein the log target processing includes encryption processing of encrypting the compressed log.

11. The medical equipment according to claim 1, wherein the log target processing includes processing of generating information which adds information for confirmation of integrity of the audit log.

12. The medical equipment according to claim 1, wherein the log target processing includes processing for confirmation of integrity of the audit log.

13. The medical equipment according to claim 1, wherein the log generation unit generates integrity verifying information for verification of integrity of the log and outputs to an external storage device the log and the integrity verifying information in association with each other.

14. The medical equipment according to claim 13, wherein the log generation unit generates as the integrity verifying information a confirming application which is read into a user terminal to be activated.

15. The medical equipment according to claim 13, wherein the log generation unit generates as the integrity verifying information a confirming application which allows a user terminal to function as a log integrity confirming section which verifies integrity of the log stored in the external storage device.

16. The medical equipment according to claim 13, wherein the log generation unit generates as the integrity verifying information a confirming application which allows a user terminal to function as a log configuration confirming section which judges whether a configuration of the log stored in the external storage device is complete and as a log integrity confirming section which verifies integrity of the log stored in the external storage device.

17. The medical equipment according to claim 13, wherein the log generation unit executes encryption processing of encrypting the log and verifying information generation processing of generating as the integrity verifying information a confirming application configured to decrypt the log when it is read into a user terminal to be activated.

18. The medical equipment according to claim 13, wherein the log generation unit generates the integrity verifying information common to the logs.

19. The medical equipment according to claim 13, wherein the log generation unit generates log integrity verifying information used to verify integrity of the log, and the log management unit confirms the log integrity verifying information with respect to the log, thereby verifying integrity of the log.

20. The medical equipment according to claim 13, wherein the log generation unit creates a first message digest to generate the log integrity verifying information by using a character string based on a calculation utilizing a hash function, and the log management unit creates a second message digest to generate the integrity verifying information by executing a calculation utilizing a hash function which employs a character string which is equal to or different from the character string used by the log generation unit.

21. The medical equipment according to claim 13, wherein the log management unit adds information indicating that integrity has not been confirmed to the log whose integrity has not been confirmed.

22. The medical equipment according to claim 13, wherein the log management unit supplies to a display device information indicating that integrity has not been confirmed with respect to the log whose integrity has not been confirmed, thereby displaying the supplied information.

* * * * *